(12) United States Patent
Gloss et al.

(10) Patent No.: US 11,583,401 B2
(45) Date of Patent: Feb. 21, 2023

(54) HEART VALVE REPAIR

(71) Applicant: Medtronic Vascular, Inc., Santa Rosa, CA (US)

(72) Inventors: Michael Gloss, Minneapolis, MN (US); Caitlin Dorff, Santa Rosa, CA (US); Fatemeh Fatemi Far, Santa Rosa, CA (US); Emily Grimm, Petaluma, CA (US); Matthew E. Genovese, Windsor, CA (US); Olivia Metcalf, Santa Rosa, CA (US); Karan Punga, San Rafael, CA (US); Eric Pierce, Mission Viejo, CA (US)

(73) Assignee: MEDTRONIC VASCULAR, INC., Santa Rosa, CA (US)

( * ) Notice: Subject to any disclaimer, the term of this patent is extended or adjusted under 35 U.S.C. 154(b) by 439 days.

(21) Appl. No.: 16/710,927

(22) Filed: Dec. 11, 2019

(65) Prior Publication Data

US 2020/0188107 A1 Jun. 18, 2020

Related U.S. Application Data

(60) Provisional application No. 62/779,310, filed on Dec. 13, 2018.

(51) Int. Cl.
*A61F 2/24* (2006.01)
*A61B 17/00* (2006.01)
*A61F 2/95* (2013.01)

(52) U.S. Cl.
CPC ...... *A61F 2/2436* (2013.01); *A61B 17/00234* (2013.01); *A61B 2017/00243* (2013.01); *A61B 2017/00323* (2013.01); *A61F 2/9517* (2020.05); *A61F 2220/0016* (2013.01)

(58) Field of Classification Search
CPC ...... A61F 2/2436; A61F 2/9517; A61F 2/246; A61F 2/2454; A61F 2/2469; A61F 2/2478; A61F 2/2457; A61F 2220/0016; A61B 17/00234; A61B 17/1285; A61B 2017/00323
See application file for complete search history.

(56) References Cited

U.S. PATENT DOCUMENTS

| | | | |
|---|---|---|---|
| 7,563,267 B2 * | 7/2009 | Goldfarb | A61B 17/0469 606/151 |
| 2003/0083742 A1 | 5/2003 | Spence et al. | |
| 2003/0105473 A1 * | 6/2003 | Miller | A61B 17/068 606/139 |

(Continued)

OTHER PUBLICATIONS

International Search Report and Written Opinion of International Application No. PCT/US2019/065843, dated Feb. 11, 2020, 10 pp.

(Continued)

*Primary Examiner* — Erich G Herbermann
(74) *Attorney, Agent, or Firm* — Medler Ferro Woodhouse & Mills PLLC

(57) ABSTRACT

An example medical system includes a medical device configured to join the edges of the leaflets together, an elongate body configured to be navigated through vasculature to a heart valve of patient, and a plurality of tissue engagement devices extending from a distal end of the elongate body, each tissue engagement device comprising at least one clamp configured to capture leaflets of the heart valve.

11 Claims, 30 Drawing Sheets

(56) References Cited

U.S. PATENT DOCUMENTS

| | | | |
|---|---|---|---|
| 2004/0167573 A1* | 8/2004 | Williamson, IV | ............................ A61B 17/0469 606/221 |
| 2008/0255427 A1* | 10/2008 | Satake | ................... A61B 17/08 606/205 |
| 2010/0022823 A1 | 1/2010 | Goldfarb et al. | |
| 2010/0292785 A1* | 11/2010 | Seguin | ............... A61B 17/0401 623/2.11 |
| 2010/0298929 A1 | 11/2010 | Thornton et al. | |
| 2011/0137397 A1* | 6/2011 | Chau | ..................... A61F 2/2409 623/2.37 |
| 2013/0066341 A1* | 3/2013 | Ketai | ................... A61F 2/2466 606/151 |
| 2013/0325038 A1* | 12/2013 | Sato | ................... A61B 17/3468 606/139 |
| 2015/0257878 A1* | 9/2015 | Lane | .................... A61F 2/2427 623/2.19 |
| 2016/0008129 A1 | 1/2016 | Siegel | |

OTHER PUBLICATIONS

Extended European Search Report; EP Application No. 19895216.0; dated Aug. 9, 2022.

\* cited by examiner

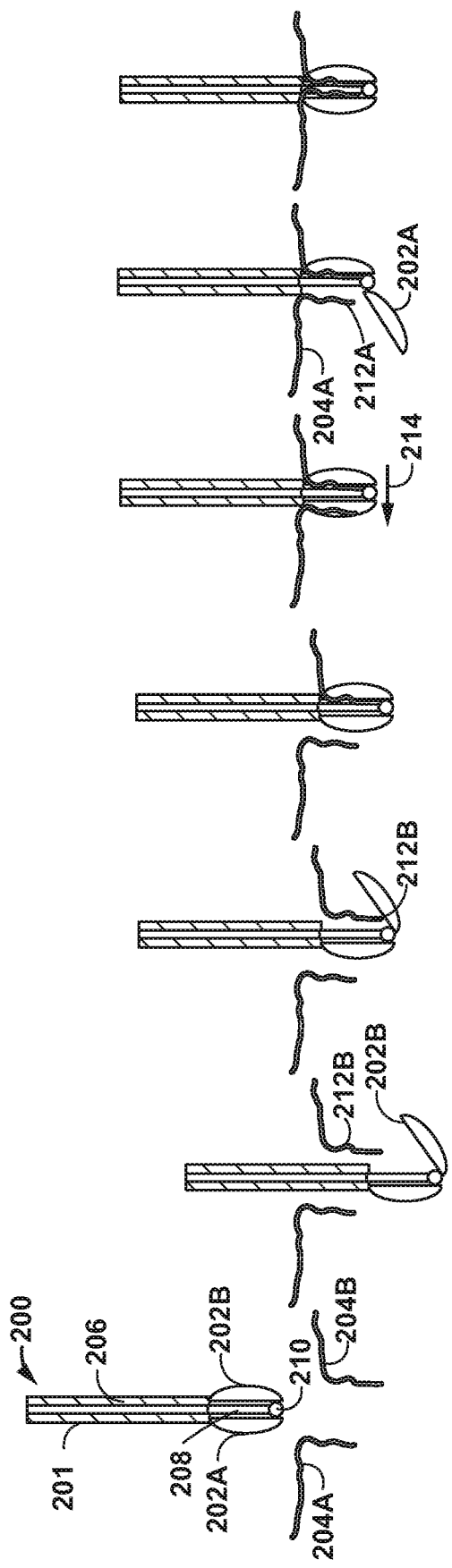

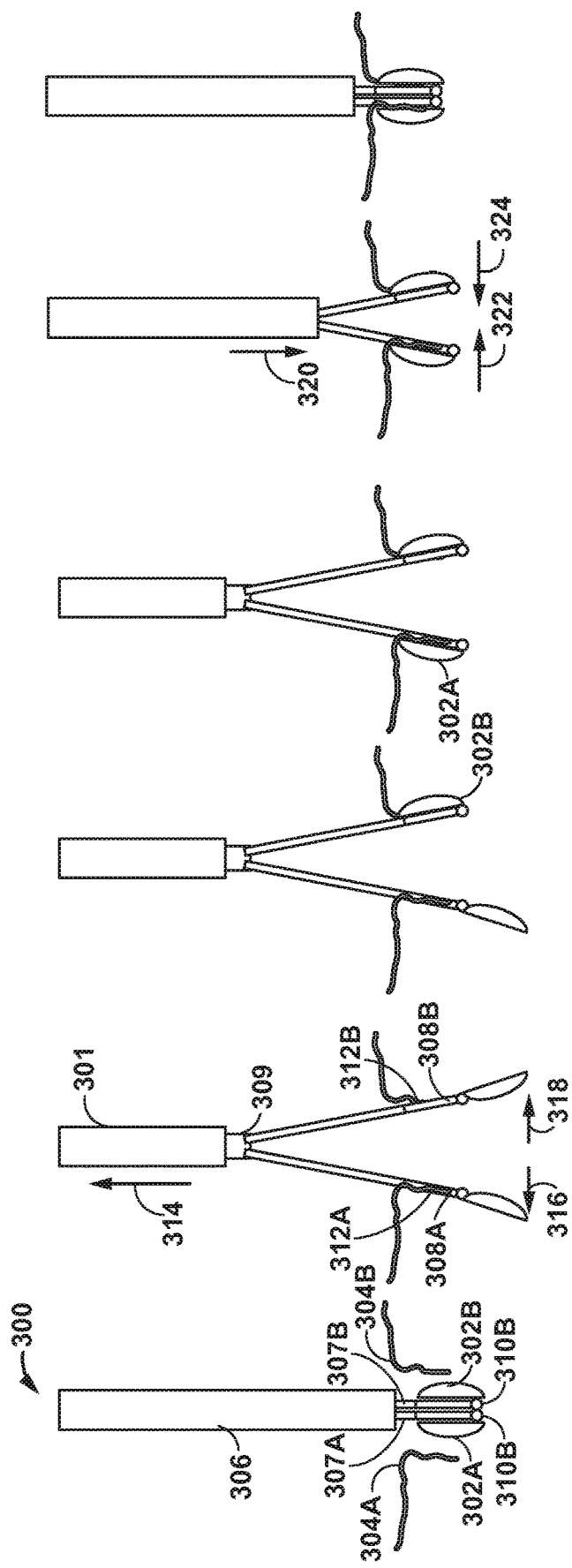

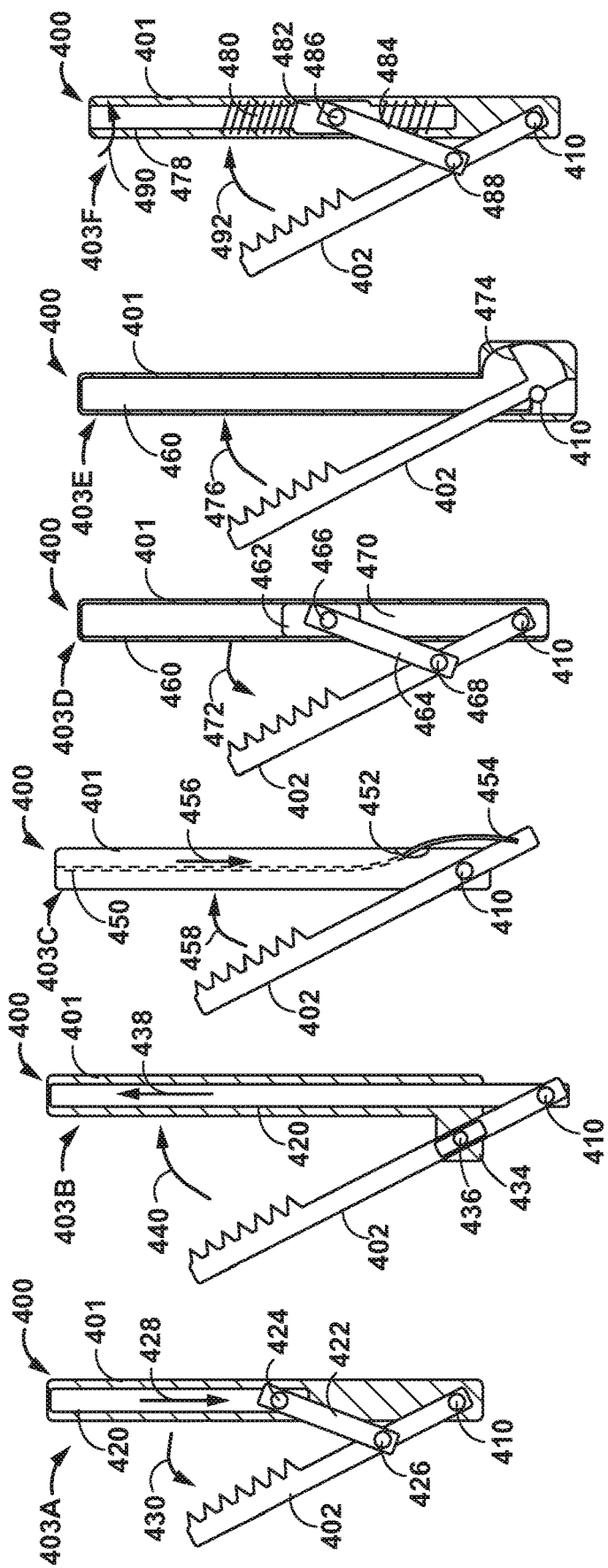

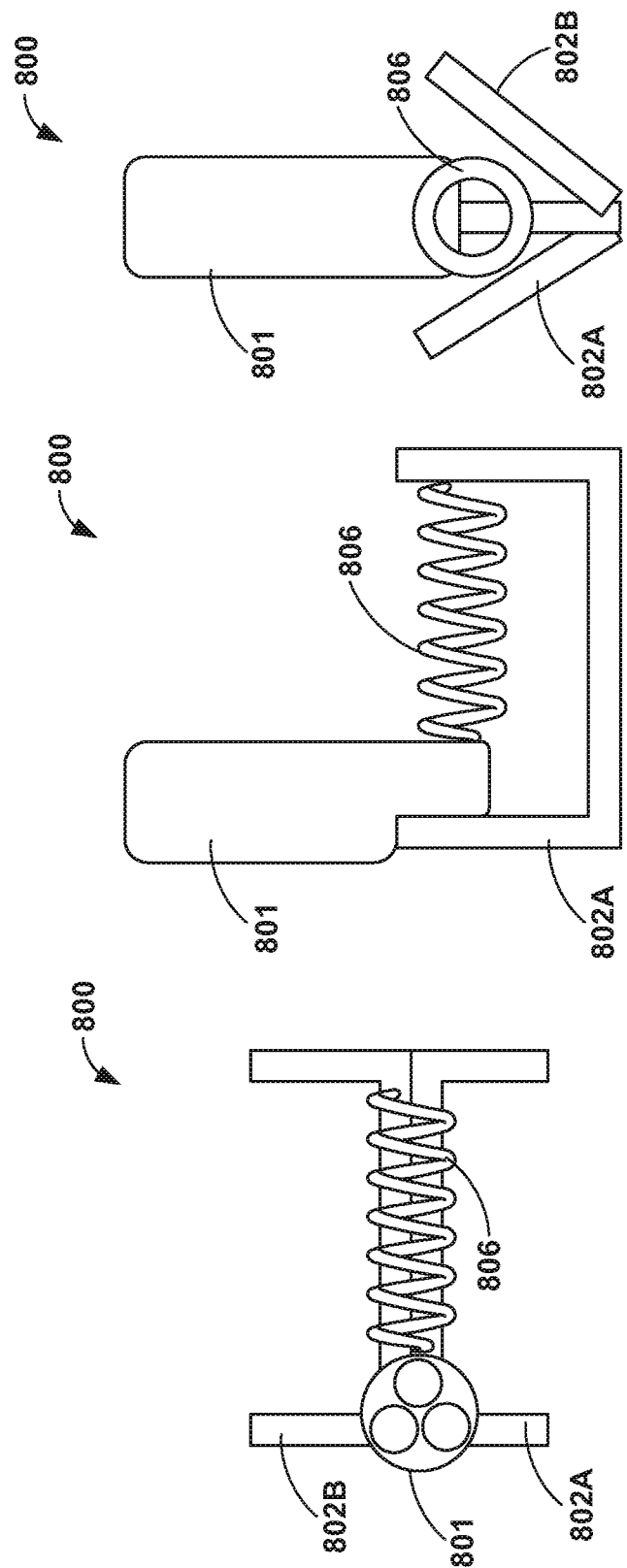

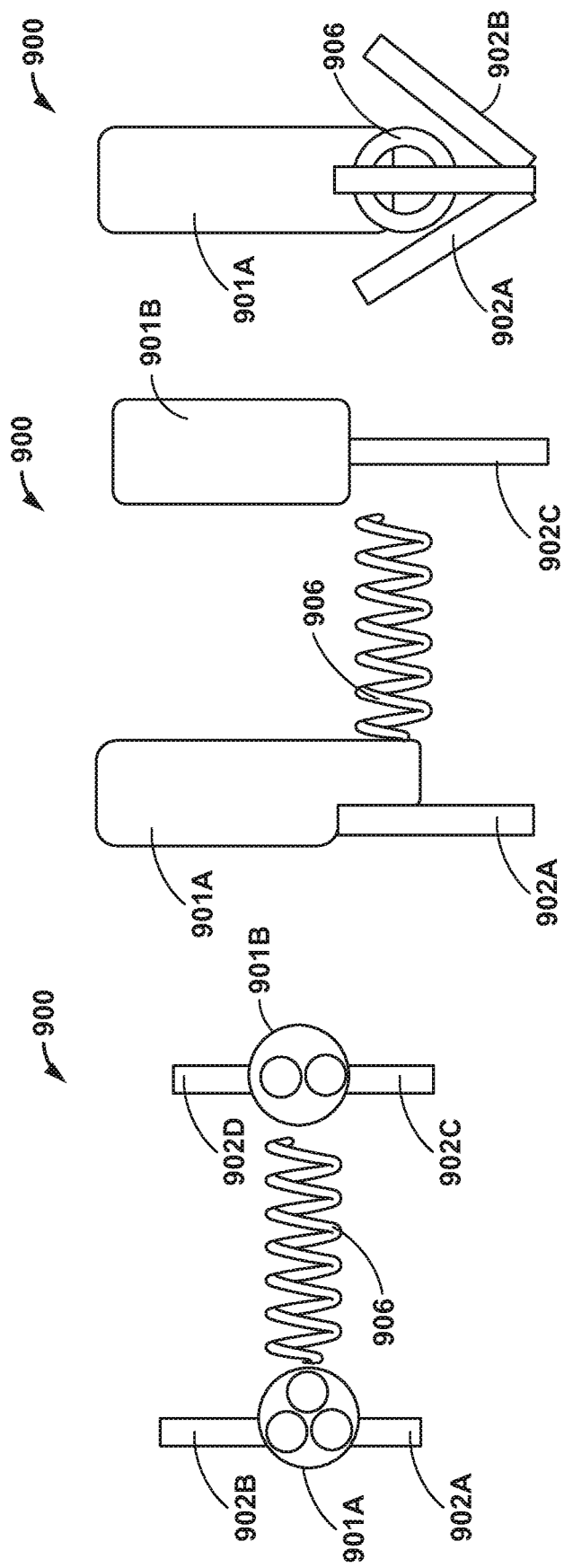

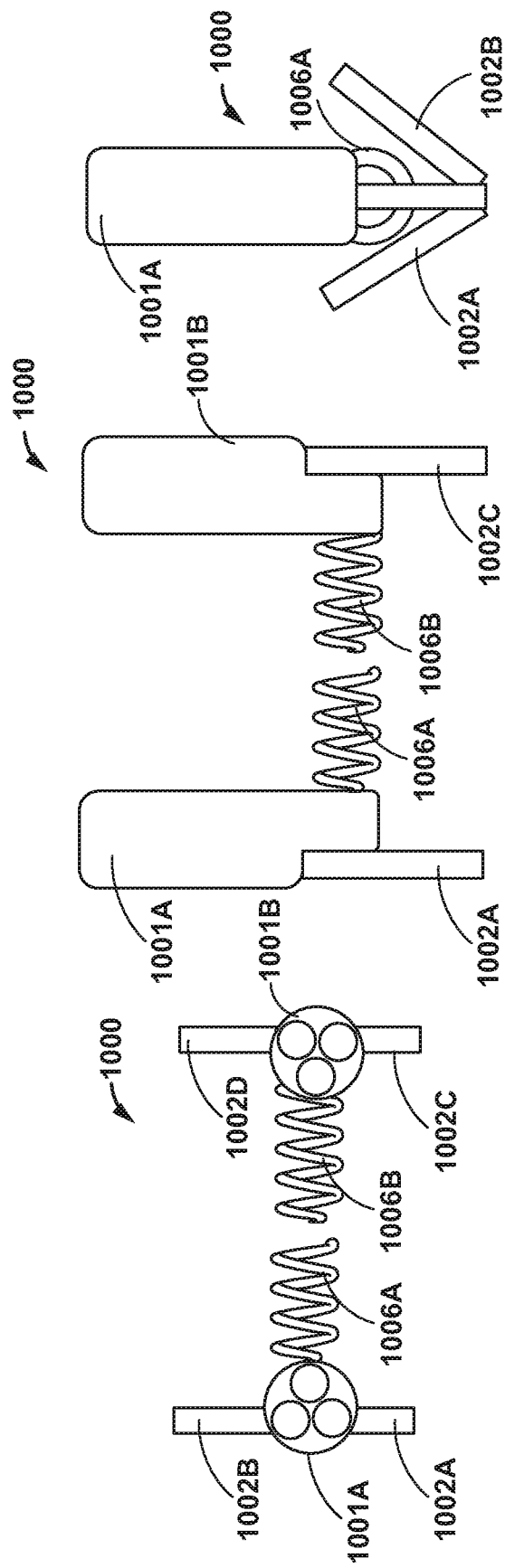

HEART VALVE REPAIR

This application claims the benefit of U.S. Provisional Patent Application Ser. No. 62/779,310, filed on Dec. 13, 2018, the entire content of which is incorporated by reference herein.

TECHNICAL FIELD

This disclosure relates to heart valve repair, such as mitral valve repair.

BACKGROUND

Some patient conditions can produce valvular insufficiency or regurgitation in a heart of the patient. Valvular insufficiency or regurgitation occurs when a valve in a heart of a subject does not close completely, allowing blood to flow backwards (e.g., from the left ventricle to the left atrium), which may adversely impact the functionality of the heart.

The mitral valve includes two leaflets (anterior and posterior) attached to an annulus (e.g., a fibrous ring). In a healthy heart, the mitral valve leaflets close during contraction of the left ventricle and prevent blood from flowing back into the left atrium. Mitral valve regurgitation is a condition in which the leaflets of a mitral valve of a subject do not coapt properly and, as a result, blood regurgitates back into the left atrium from the left ventricle. The regurgitation of blood back into the left atrium may result in a reduced ejection volume from the left ventricle, causing the heart of the subject to work relatively hard to supply the desirable volume of blood to the body. Mitral regurgitation may occur because of different patient conditions. For example, secondary mitral regurgitation, also referred to as functional mitral regurgitation, may occur when a left ventricle dilates and causes dilation of the mitral annulus of a subject.

SUMMARY

The present disclosure describes tissue compression devices, systems, and techniques that can be used to help engage tissue, such as leaflets of a heart valve, in order to implant a medical device configured to treat valve regurgitation. The devices, systems, and techniques described herein may be used to treat mitral valve regurgitation or other patient conditions that involve valves.

In some aspects, this disclosure describes example delivery devices including an elongate body and a plurality of tissue engagement devices extending from the elongate body, each tissue engagement device including at least one clamp configured to engage tissue and at least one actuation member configured to move the at least one clamp from an open configuration to a closed configuration.

In some aspects, this disclosure describes example medical systems that include a medical device configured to join tissue and a catheter configured to deliver the medical to a target tissue site. The catheter may include a handle having a control member, an elongate body extending along a longitudinal axis from a proximal end coupled to the handle to a distal end, and a plurality of tissue engagement devices. Each tissue engagement device may include at least one clamp configured to engage tissue and at least one actuation member controllable at the control member and configured to move the at least one clamp from an open configuration to a closed configuration.

The details of one or more examples are set forth in the accompanying drawings and the description below. Other features, objects, and advantages will be apparent from the description and drawings, and from the claims.

BRIEF DESCRIPTION OF DRAWINGS

FIGS. 2A-2G are conceptual diagrams illustrating an example delivery device and an example method of using the delivery device to deliver and secure the clamps to leaflets of a heart valve.

FIGS. 3A-3F are conceptual diagrams illustrating another example delivery device and an example method of using the delivery device to deliver and secure clamps to leaflets of a heart valve.

FIG. 4A-4F are conceptual diagrams illustrating example actuation mechanisms of a delivery device configured to move a clamp from an open configuration to a closed configuration and/or from a closed configuration to an open configuration.

FIGS. 8A-8C are conceptual diagrams illustrating an example delivery system including a catheter, clamps, and a coil.

FIGS. 9A-9C are conceptual diagrams illustrating an example delivery system including a first catheter including two clamps and configured to deliver a coil, and a second catheter including two clamps.

FIGS. 10A-10C are conceptual diagrams illustrating an example delivery system including a first catheter including two clamps, and configured to deliver a first coil, and a second catheter including two clamps, and configured to deliver a second coil.

DETAILED DESCRIPTION

This disclosure describes devices, systems, and techniques for repairing a heart valve, such as, but not limited to, a mitral valve, that are a less invasive compared to some other techniques, such as open heart surgeries. In some cases, a heart valve of a patient is repaired clamping or suturing the leaflets of the heart valve together, dividing the valve orifice into separate functioning orifices. This may be referred to as edge to edge valve repair. The devices and systems described herein may be used as part of such a medical procedure and may be used to facilitate the performing of such a medical procedure via a transcatheter technique (e.g., eliminating the need for an open heart surgery or a more invasive technique). As discussed in further detail below, the devices and systems described herein are configured to grasp the leaflets of a heart valve independently or simultaneously, such that the leaflets may be sutured, clamped, or otherwise connected together, e.g., at the edge of the leaflets. In some examples, independent leaflet grasping, may improve placement of the sutures or clamp and/or decrease the amount of time required to achieve the desired medical placement.

In examples in which a clinician uses a medical device to hold edges of leaflets of the heart valve together, the example devices and systems described herein may be used to implant such a medical device in a heart of a patient via a transcatheter procedure. Additionally, or alternatively, the disclosed devices, systems, and techniques may enable assessing functionality of the medical device while still having the ability to reposition or retrieve the medical device. Assessing functionally of the medical device while still being able to reposition or retrieve the medical device may improve effectiveness of the treatment.

Edge to edge heart valve repair may be useful for treating heart valve regurgitation, e.g., for patients with relatively normal leaflet motion (compared to a healthy heart that does not have degenerative mitral regurgitation) and/or with a dilated annulus or leaflet prolapse. Leaflet prolapse may be due to chordal rupture or papillary muscle elongation. While some regurgitation may persist after an edge to edge heart valve repair, the edge to edge heart valve repair may be sufficient to minimize the regurgitation enough to slow or even halt further progression into heart failure.

Figure 1A:
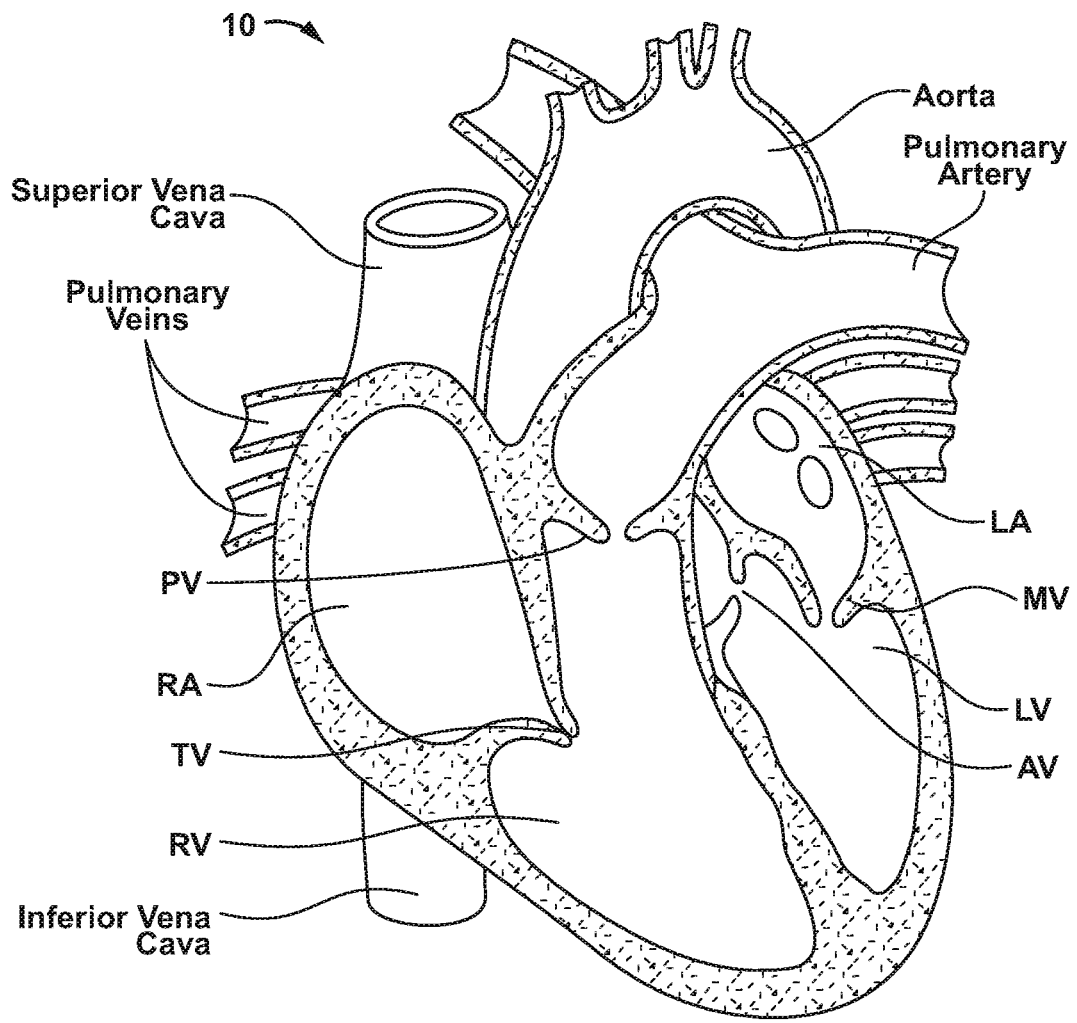
FIGS. 1A and 1B are schematic cross-sectional views of an example human heart 10.
Figure 1B:
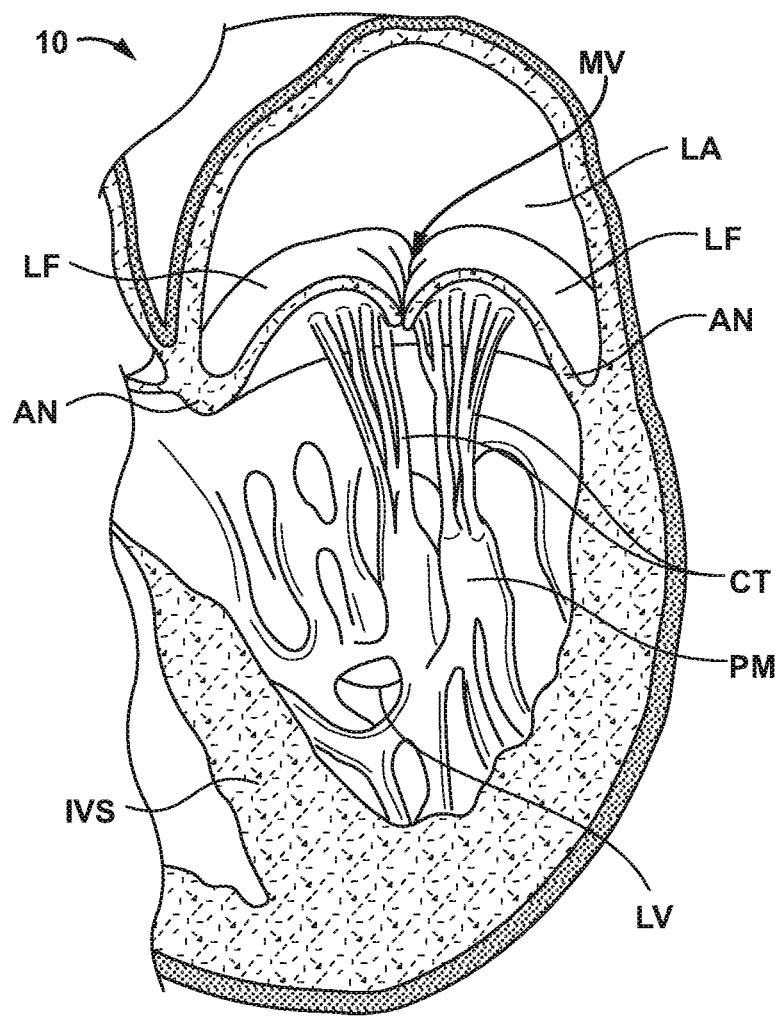

FIGS. 1A and 1B are schematic cross-sectional views of an example human heart 10. The human heart 10 is a four chambered, muscular organ that provides blood circulation through the body during a cardiac cycle. The four main chambers include the right atrium (RA) and right ventricle (RV) which supplies the pulmonary circulation, and the left atrium (LA) and left ventricle (LV) which supplies oxygenated blood received from the lungs to the remaining body. To ensure that blood flows in one direction through the heart, atrioventricular valves (tricuspid valve (TV) and mitral valves (MV)) are present between the junctions of the atrium and the ventricles, and semi-lunar valves (pulmonary valve (PV) and aortic valve (AV)) govern the exits of the ventricles leading to the lungs and the rest of the body. These valves contain leaflets (LF) or cusps that open and shut in response to blood pressure changes caused by the contraction and relaxation of the heart chambers. FIG. 1B is a schematic sectional illustration of a left ventricle LV of heart 10 showing anatomical structures and a native mitral valve MV.

The left atrium LA receives oxygenated blood from the lungs via the pulmonary veins and pumps the oxygenated blood through the mitral valve MV and into the left ventricle LV during ventricular diastole. The left ventricle LV contracts during systole and blood flows outwardly through the aortic valve AV, into the aorta and to the remainder of the body. In a healthy heart, the leaflets LF of the native mitral valve MV meet evenly at the free edges or "coapt" to close and prevent back flow of blood into the left atrium LA during contraction of the left ventricle LV. The tissue of the leaflets LF attach to the surrounding heart structure via a dense fibrous ring of connective tissue called an annulus AN. The flexible tissue of the leaflets LF of the native mitral valve MV are connected to papillary muscles PM, which extend upwardly from the lower wall of the left ventricle LV and the interventricular septum IVS, via branching tendons called chordae tendinae CT.

Mitral valve regurgitation is a condition in which the leaflets of a mitral valve of a subject do not coapt properly and, as a result, blood regurgitates back into the left atrium LA from the left ventricle LV. The regurgitation of blood back into the left atrium LA may result in a reduced ejection volume from the left ventricle LV, causing the heart of the subject to work relatively hard to supply the desirable volume of blood to the body. Mitral regurgitation may occur because of one or more patient conditions. For example, secondary mitral regurgitation, also referred to as functional mitral regurgitation, may occur when the left ventricle LV dilates and causes dilation of the mitral annulus of a patient. The leaflets LF of the valves may move apart as a result of the dilation of the left ventricle LV, which may adversely impact the ability of the leaflets to properly coapt.

In addition to or instead of being caused by dilation of the left ventricle LV, mitral valve regurgitation (or other valve regurgitation) may be caused by calcified plaque buildup in heart 10. For example, the leaflets LF of the valves (e.g., aortic valve AV or mitral valve MV) may harden and may not sufficiently coapt or meet, such that regurgitation may occur where the valve does not close completely, allowing blood to flow backwards (e.g., from the left ventricle LV to the left atrium LA). The left side of heart 10 (e.g., mitral valve MV and aortic valve AV) can be more likely to become calcified because of the higher pressures generated.

The medical devices, systems, and techniques described herein may be used to repair a valve of heart 10 via a minimally invasive medical procedure, e.g., via a transcatheter, trans-septal medical procedure that is less invasive than open heart surgery. While open heart surgeries, such as annuloplasty performed via open heart surgery, may have positive outcomes, a more minimally invasive medical procedure may also be associated with positive outcomes, as well as a shorter recovery time for some patients compared to open heart surgery. While the devices, systems, and techniques are primarily described herein with reference to mitral valve repair, in other examples, the devices, systems, and techniques described herein can be used to repair other heart valves or other valves outside of the heart of a patient.

FIGS. 2A-2G are conceptual diagrams illustrating an example delivery device 200 and an example method of using delivery device 200 to deliver and secure clamps 202A and 202B (collectively, "clamps 202") to anterior leaflet 204A and posterior leaflet 204B (collectively, "leaflets 204") of mitral valve MV of heart 10. Clamps 202 are examples of a medical device that can be used to hold edges of leaflets 204 of mitral valve MV together in order to help treat valvular insufficiency or regurgitation. As illustrated in FIG. 2A, in some examples, delivery device 200 may include a single-arm catheter 201 that is configured to be introduced into the vasculature of the patient and steered through the vasculature to the left atrium LA of heart 10. Although illustrated as clamping leaflets of mitral valve MV, delivery device 200 may be used to clamp other heart valves or tissues within a patient.

Delivery device 200 may include a handle (not shown) and an elongate body 206. The handle includes control members operatively coupled via one or more control wires 208 to clamps 202. Clamps 202 may be coupled to one or more hinges 210 to enable clamps 202 to move between an open configuration and a closed configuration. In an open configuration of each clamp 202, an end of the clamp (e.g., the proximal end in the example shown in FIG. 2A) is away from elongate body 206, and in the closed configuration, the end of the clamp is closer to elongate body 206, as shown in FIG. 2A. Hinge 210 may include any suitable mechanical hinge or region of flexible material. In this way, the control wire 208 may be used to open clamps 202 to an open configuration or close clamps 202 to a closed configuration. Control wires 208 are any suitable control mechanism that can be used to move clamps 202 from the open configuration to the closed configuration, or vice versa, and may be formed from a material other than wire in other examples.

As illustrated in FIG. 2B, in some examples, clamps 202 may be individually actuated. For example, a clinician may manipulate control wire 208 to open clamp 202B into an open configuration, an example of which is shown in FIG. 2B. As illustrated in FIG. 2C, clamp 202B in the open configuration may be positioned proximate to posterior leaflet 204B to capture an edge 212B of posterior leaflet 204B. After being positioned proximate to posterior leaflet 204B, a clinician may use one or more control wires 208 to move clamp 202B into the closed configuration to capture edge 212B of posterior leaflet 204B, as illustrated in FIG. 2D. In some examples, clamps 202 may include features configured to improve engagement of a respective leaflet edge 212A, 212B. For example, clamps may include barb-like features (e.g., tines, protrusions, surface roughening, and the like), a tacky material configured to removably adhere to tissue, apertures configured to provide suction, or the like.

After capturing edge 212B of posterior leaflet 212B, delivery device 200 may be positioned to capture an edge 212A of anterior leaflet 204A. For example, as illustrated in FIG. 2E, a clinician may move delivery device 200 in the direction of arrow 214 to be closer to anterior leaflet 204A. In some examples, the clinician may push anterior leaflet 204A against clamp 202A. Once in the desired positioned relative to leaflet 204A (which may or may not require adjusting the position of delivery device 200), the clinician may use control wire 208 to open clamp 202A into an open configuration, as illustrated in FIG. 2F. As illustrated in FIG. 2G, after being positioned, clamp 202A may be closed into the closed configuration to capture edge 212A of anterior leaflet 204A.

In some examples, after capturing both of anterior leaflet 204A and posterior leaflet 204B, a retention device, such as a coil or u-clip, or a suture that is configured to hold edge 212A and edge 212B together, may be delivered to the mitral valve via catheter 201 or via another catheter. After the retention device or suture is in place to hold leaflets 212A, 212B together, clamps 202 may be opened, and single-arm catheter 201 be withdrawn from the vasculature of the patient, alone or along with clamps 202.

In some examples, clamps 202A, 200B are mechanically connected together such that clamps 202A, 202B may be used as a chronically implanted medical device that holds valve leaflets 212A, 212B together and turns a single orifice of the mitral valve MV into two separate orifices. This may be referred to as edge to edge repair and may be used to help reduce mitral valve regurgitation or at least slow down the worsening of the mitral valve regurgitation.

In some examples, single-arm catheter 201 may be configured to decouple from clamps 202. For example, after the clinician uses delivery device 200 to capture both anterior leaflet 204A and posterior leaflet 204B using the respective clamp 202A, 20B, the clinician may decouple catheter 201 from clamps 202. Clamps 202 may remain in place in heart 10 and hold leaflets 204A, 204B together. Thereafter, single-arm catheter 201 may be withdrawn from the vasculature of the patient, leaving clamps 202 in place.

In some examples, compared to single-arm catheter 201, a two-arm catheter may be configured to produce more force to pull a clamped posterior leaflet 204B to anterior leaflet 204A to clamp the anterior leaflet 204A. FIGS. 3A-3F are conceptual diagrams illustrating an example delivery device 300 and an example method of using delivery device 300 to deliver and secure clamps 302A and 302B (collectively, "clamps 302") to anterior leaflet 304A and posterior leaflet 304B (collectively, "leaflets 304") of mitral valve MV of heart 10. Delivery device 300 may be the same as or substantially similar to delivery device 200 describe above, except for the differences described herein.

As illustrated in FIG. 3A, delivery device 300 may include a two-arm catheter 309 that is configured to be introduced in to the vasculature of the patient and steered through the vasculature to the left atrium LA of heart 10. Two-arm catheter 309 includes a first arm 307A and a second arm 307B (collectively, "arms 307"). Arms 307 include, respectively, a first clamp 302A and a second clamp 302B (collectively, "clamps 302"). In some examples, medical device may include a multi-arm catheter having more than two arms, such as four arms or six arms. In some examples, delivery device 300 may include a handle (not shown) having control members operatively coupled via control wires 308A and 308B (collectively, "control wires 308") to respective clamps 302 to move clamps 302 to an open configuration or to move clamps 302 to a closed configuration. In some examples, respective clamps 302 may be coupled to one or more respective hinges 310A and 310B (collectively, "hinges 310") to enable clamps 302 to open and close. Hinges 310 may include any suitable mechanical hinge or region of flexible material.

As illustrated in FIG. 3B, before or after opening clamps 302, an outer sheath 301 of delivery device 300 may be withdrawn in the proximal direction to expose arms 307. Additionally, or alternatively, two-arm catheter 309 may be extended in the distal direction, relative to sheath 301. In some examples, arms 307 may be configured to change position in response to outer sheath 301 being withdrawn. For example, arms 307 may include a shape-memory alloy having an undeformed shape extending away from a central longitudinal axis of elongate body 306 at a selected angle. When loaded into sheath 301, sheath 301 may apply a constraining force on arms 307 and hold arms 307 in a collapsed configuration in which arms 307 are substantially parallel to the central longitudinal axis of elongate body 306. Arms 307 may be biased outwards such that upon withdrawing sheath in a proximal direction 314, first arm 307A may move in an anterior direction 316 toward anterior leaflet 304A. Similarly, second arm 307B may move in a posterior direction 318 toward posterior leaflet 304B. In some examples, the movement of arms 307 may be predetermined to position respective clamps 302 adjacent to leaflet edges 312A and 312B.

A clinician may withdraw sheath 301 to the extent necessary to position clamps 302A, 302B proximate to the respective leaflets 304A, 304B to grab onto leaflets 304A, 304B. For example, distal ends of arms 307 may be configured to extend furthest away from the central longitudinal axis of elongate body 306 when sheath 301 is fully retracted away from the proximal ends of arms 307. Thus, when sheath 301 is moved from the fully retracted position in a distal direction, sheath 301 may compress arms 307 towards the central longitudinal axis of elongate body 306. The clinician may therefore, modify the distance by which the distal ends of arms 307 are separated from each other (in a direction orthogonal to the central longitudinal axis of elongate body 306) by modifying the amount by which sheath 301 is retracted in a proximal direction. The clinician may wish to modify the distance by which the distal ends of arms 307 are separated from each other in order to better position clamps 302 adjacent the respective leaflets 304A, 304B.

In some examples described herein, clamps described herein, including clamps 302, may be radiopaque or include radiopaque markers so that a clinician can determine the location of clamps within heart 10 based on a radiographic image. In addition, in some examples, the radiopacity of a clamp may permit the clinician to determine whether the clamp is in the open or closed configuration.

The configuration of clamps 302 may be individual controlled. For example, after clamp 302B is positioned proximate leaflet 304A, control wire 308B may be used to close move clamp 302B from the open configuration into the closed configuration to capture edge 312B of posterior leaflet 304B, as illustrated in FIG. 3C. Similarly, as illustrated in FIG. 3D, control wire 308A may be used to move clamp 302A from the open configuration into the closed configuration to capture edge 312A of anterior leaflet 304A. After capturing both anterior leaflet 304A and posterior leaflet 304B, sheath 301 may be move in the distal direction to bring clamps 302 closer together and into engagement with each other. Alternatively, or additionally, two-arm catheter may be move proximally relative to sheath 301 to bring clamps 302 into engagement. After bringing claims 302 into engagement, clamps may be mechanically coupled to each other, for example, by a mechanical interlock, suture, or the like.

In some examples, after capturing both of anterior leaflet 304A and posterior leaflet 304B, a clinician may deliver a retention device through catheter 301 or via another catheter, the retention device being configured to hold edge 312A and edge 312B together. After delivering the retention device or suture, clamps 302 may be opened, and catheter 301 be withdrawn from the vasculature of the patient, alone or along with clamps 302.

In some examples, after mechanically coupling clamps 302, clamps 302 are left in place and act as the retention device. Two-arm catheter 301 may be configured to decouple from clamps 302 and withdrawn from the vasculature of the patient, leaving clamps 302 in place.

Although describe in FIGS. 2A-3F as actuated by a control wire, clamps described herein may be actuated by any suitable actuation mechanism, such as, but not limited to, bar linkages, hydraulics, pull elements (e.g., wires, rods, or cords). FIG. 4A-4F are conceptual diagrams illustrating example actuation mechanisms 403A-403F (collectively, "actuation mechanisms 403") of an example delivery device 400 (e.g., at a distal end of an arm of a catheter 401) configured to move a clamp 402 from an open configuration to a closed configuration and/or from a closed configuration to an open configuration.

As illustrated in FIG. 4A, clamp 402 may be coupled to catheter 401 at hinge 410. Actuation mechanism 403A include an inner member 420 in sliding engagement with a lumen of catheter 401. Inner member 420 may be coupled to a hinge arm 422 via hinges 424 and 426. Inner member 420 is controllable at the handle (not shown) of delivery device 400 such that extending inner member 420 in the distal direction (e.g., in the direction arrow 428) relative to catheter 401 may result in movement of clamp 402 (e.g., in the direction of arrow 430) toward an open configuration. In some examples, movement of inner member 420 in a proximal direction may result in movement of clamp 402 toward a closed configuration.

As illustrated in FIG. 4B, actuation mechanism 403B includes an inner member 420 in sliding engagement with a lumen of catheter 401. Clamp 402 may be coupled to inner member 420 at hinge 432. Catheter 401 may include an L-shaped portion 434 extending at an angle, such as perpendicular, from a longitudinal axis of catheter 401. Clamp 402 may be coupled to L-shaped portion 434 at a hinge 436. Inner member 420 is controllable at the handle (not shown) of delivery device 400 such that extending inner member 420 in the proximal direction (e.g., in the direction arrow 438) relative to catheter 401 results in movement of clamp 402 (e.g., in the direction of arrow 440) toward a closed configuration. In some examples, movement of inner member 420 in a distal direction results in movement of clamp 402 toward an open configuration.

As illustrated in FIG. 4C, clamp 402 may be coupled to catheter 401 at hinge 410. Actuation mechanism 403C includes a wire 450 in sliding engagement with a lumen of catheter 401. Wire 450 may extend through an aperture 452 defined by catheter 401. A portion (e.g., a distal end 454) of wire 450 may be coupled to clamp 402. Wire 450 may be controllable at the handle (not shown) of delivery device 400 such that moving wire 450 in the distal direction (e.g., in the direction arrow 456) relative to catheter 401 may result in movement of clamp 402 (e.g., in the direction of arrow 458) toward a closed configuration. In some examples, moving wire 450 in a proximal direction may result in movement of clamp 402 toward an open configuration.

As illustrated in FIG. 4D, clamp 402 may be coupled to catheter 401 at hinge 410. Actuation mechanism 403D includes a hydraulic fluid chamber 460 within a lumen of catheter 401 and a plunger 462 defining a distal end of hydraulic fluid chamber 460. Plunger 462 may be coupled to a hinge arm 464 via hinges 466 and 468. Plunger 462 is controllable at the handle (not shown) of delivery device 400 by introducing or extracting a hydraulic fluid into or from hydraulic fluid chamber 460. For example, introducing the hydraulic fluid into hydraulic fluid chamber 460 may result in movement of plunger 462 in the distal direction (e.g., in the direction arrow 470) relative to catheter 401 may result in movement of clamp 402 (e.g., in the direction of arrow 472) toward an open configuration. In some examples, extracting the hydraulic fluid from hydraulic fluid chamber 460 may result in movement of plunger 462 in the proximal direction to movement of clamp 402 toward a closed configuration.

As illustrated in FIG. 4E, clamp 402 may be coupled to catheter 401 at hinge 410. Actuation mechanism 403E includes a hydraulic fluid chamber 460 within a lumen of catheter 401 and a hydraulic gear 474 at a distal end of hydraulic fluid chamber 460. Hydraulic gear 474 is controllable at the handle (not shown) of delivery device 400 by introducing or extracting a hydraulic fluid into or from hydraulic fluid chamber 460. For example, introducing the hydraulic fluid into hydraulic fluid chamber 460 may result in movement of hydraulic gear 474 to cause clamp 402 to pivot around hinge 410 to move (e.g., in the direction of arrow 476) toward a closed configuration. In some examples, extracting the hydraulic fluid from hydraulic fluid chamber 460 may result in movement of clamp 402 toward an open configuration.

As illustrated in FIG. 4F, clamp 402 may be coupled to catheter 401 at hinge 410. Actuation mechanism 403F includes an inner member 478 having a scroll gear 480 mechanically engaged with a collar 482. Collar 482 may be coupled to a hinge arm 484 via hinges 486 and 488. Collar 482 is controllable at the handle (not shown) of delivery device 400 by rotating inner member 478. For example, rotating inner member 478 in a first direction (e.g., in a clockwise direction shown by arrow 490 or in a counter-clockwise direction) may result in movement of collar 482 in the proximal direction relative to catheter 401, which may result in movement of clamp 402 (e.g., in the direction of arrow 472) toward a closed configuration. In some examples, rotating inner member 478 in a second direction opposite first direction 490 may result in movement of collar 482 in the distal direction to movement of clamp 402 toward an open configuration.

In some examples, two or more of actuation mechanisms 403, or parts of two or more of actuation mechanisms 403, may be used in combination. In some examples, delivery device 400 may include two or more of actuation mechanisms 403. For example, a first actuation mechanism may be configured to capture an anterior leaflet and a second actuation mechanism may be configured to capture a posterior leaflet.

In some examples, an actuation mechanism may include a spring member configured to hold the clamp in an open configuration or a closed configuration. A spring member may be useful in examples in which it may be desired to only require forces to act in one direction. This may be achieved by spring loading the clamp in the open or closed position and applying a force in one direction to actuate the clamp.

Figure 5A:
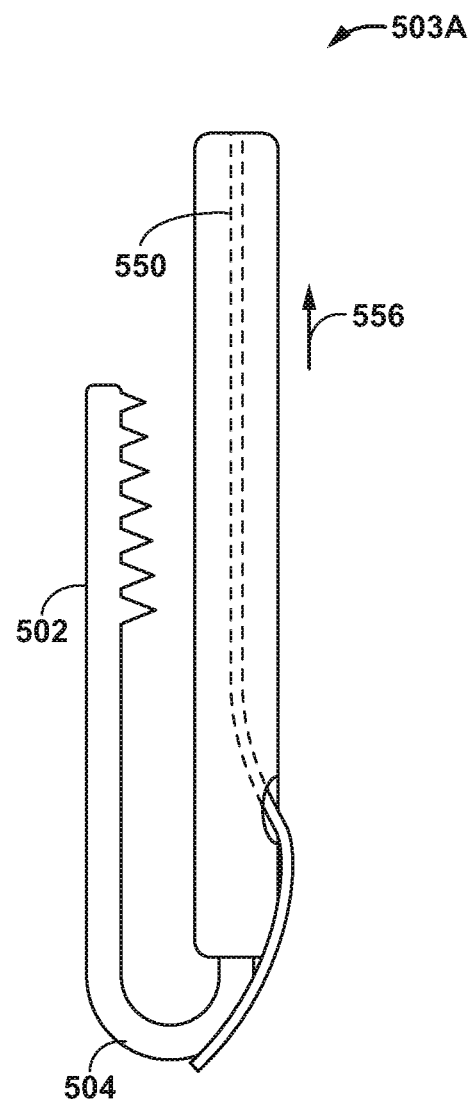
FIGS. 5A and 5B are conceptual diagrams illustrating example actuation mechanisms of a delivery device that includes a spring member configured to hold a clamp in one of an open configuration or a closed configuration.
Figure 5B:
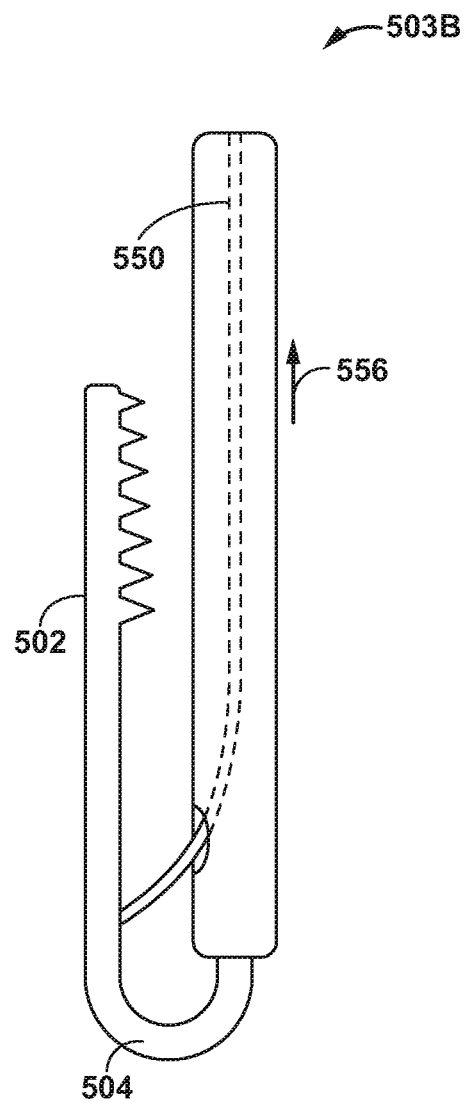

FIGS. 5A and 5B are conceptual diagrams illustrating example actuation mechanisms 503A and 503B (collectively, "actuation mechanisms 503") of a delivery device 500 that includes a respective spring member 504A and 504B configured to hold clamp 502 in one of an open configuration or a closed configuration. In response to actuation of actuation mechanism 503, e.g., pull wire 550, actuation mechanism 503 may overcome the spring force of spring member 504A, 504B to open or close clamp 502. For example, as illustrated in FIG. 5A, spring member 504A may be configured to hold clamp 502 in a closed configuration. Actuation of pull wire 550 in the proximal direction (e.g., direction of arrow 556) may overcome the spring force of spring member 504A to open clamp 502. As illustrated in FIG. 5B, spring member 504B may be configured to hold clamp 502 in an open configuration such that actuation of pull wire 550 in the proximal direction (e.g., direction of arrow 556) may overcome the spring force of spring member 504B to close clamp 502. Spring members 504A and 504B simplify respective actuation mechanisms 503A and 503B by requiring actuation of wire 550 only in one direction to cause respective actuation mechanisms 503A and 503B to move from an open configuration to a closed configuration or from a closed configuration to an open configuration.

Figure 6:
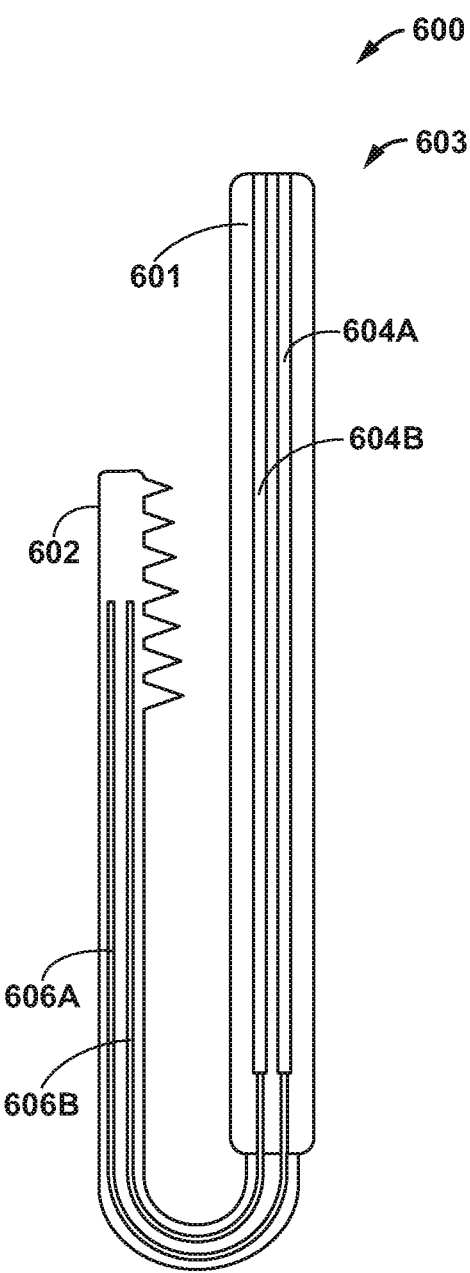
FIG. 6 is a schematic diagram illustrating an example delivery device that includes conductive electrical leads extending through catheter and an actuation mechanism configured to actuate in response to an electrical current.

In some examples, an actuation mechanism may be configured to move a clamp from a closed configuration to an open configuration and/or from an open configuration to a closed configuration in response to an electrical current. FIG. 6 is a schematic diagram illustrating an example delivery device 600 that includes electrically conductive electrical leads 604A and 604B extending through catheter 601 and an actuation mechanism 603 configured to actuate in response to an electrical current. In some examples, conductive electrical leads 604A and 604B are electrically coupled to respective conductive elements 606A and 606B that extend through at least a portion of clamp 602. Conductive elements 606A and 606B may define a resistor. An electrical current may be selectively applied to a conductive elements 606A and 606B via conductive electrical leads 604A and 604B to controllably heat clamp 602. Clamp 602 may include a shape memory alloy, such as a nickel titanium alloy, configured to have a first configuration, e.g., a closed configuration, at a first temperature and a second configuration, such as an open configuration, at a second temperature. In this way, controllably heating clamp 602 using an electrical current may be used to open and close clamp 602. In some examples, conductive electrical leads 604A and 604B may be electrically coupled to an electric motor configured to actuate clamp 602.

The clamps described in reference to FIGS. 2A-6 may be part of an implantable medical device (IMD) or part of an IMD delivery system. In examples in which a clamp is part of a medical device, the clamp may be configured to remain clamped to tissue, such as mitral valve leaflets, for at least a duration of time longer than the medical procedure used to deliver the medical device. In examples in which a clamp is part of a delivery system and removed from the heart 10 of the patient after another medical device is implanted in the heart 10, the clamp may be configured to hold the tissue together, as described above, while the medical device is deployed from the delivery system. In some examples, to enable medical device deployment after tissue clamping, the clamps may be positioned to reduce interference with placement of the medical device.

FIGS. 7A-7I are conceptual diagrams illustrating an example medical device delivery system 700 including four clamps 702A, 702B, 702C, and 702D (collectively, "clamps 702") extending from a distal end 704 thereof and configured to deploy a helical coil 706 to join tissues, such as edges of an anterior leaflet and a posterior leaflet of a mitral valve. Coil 706 can be, for example, a nitinol coil. Clamps 702 extend from respective extension members 708A, 708B, 708C, and 708D (collectively, "extension members 708"). Extension members 708 are shaped to enable helical coil 706 to pass between each of extension members 708. In some examples, clamps 702 may be individually actuated (e.g., opened and closed). For example, clamps 702 may be connected to separate actuation mechanisms. In other examples, at least some or all of the clamps 702 are configured to be simultaneously actuated. For example, these at least some clamps may be connected to the same actuation mechanism.

Figure 7A:
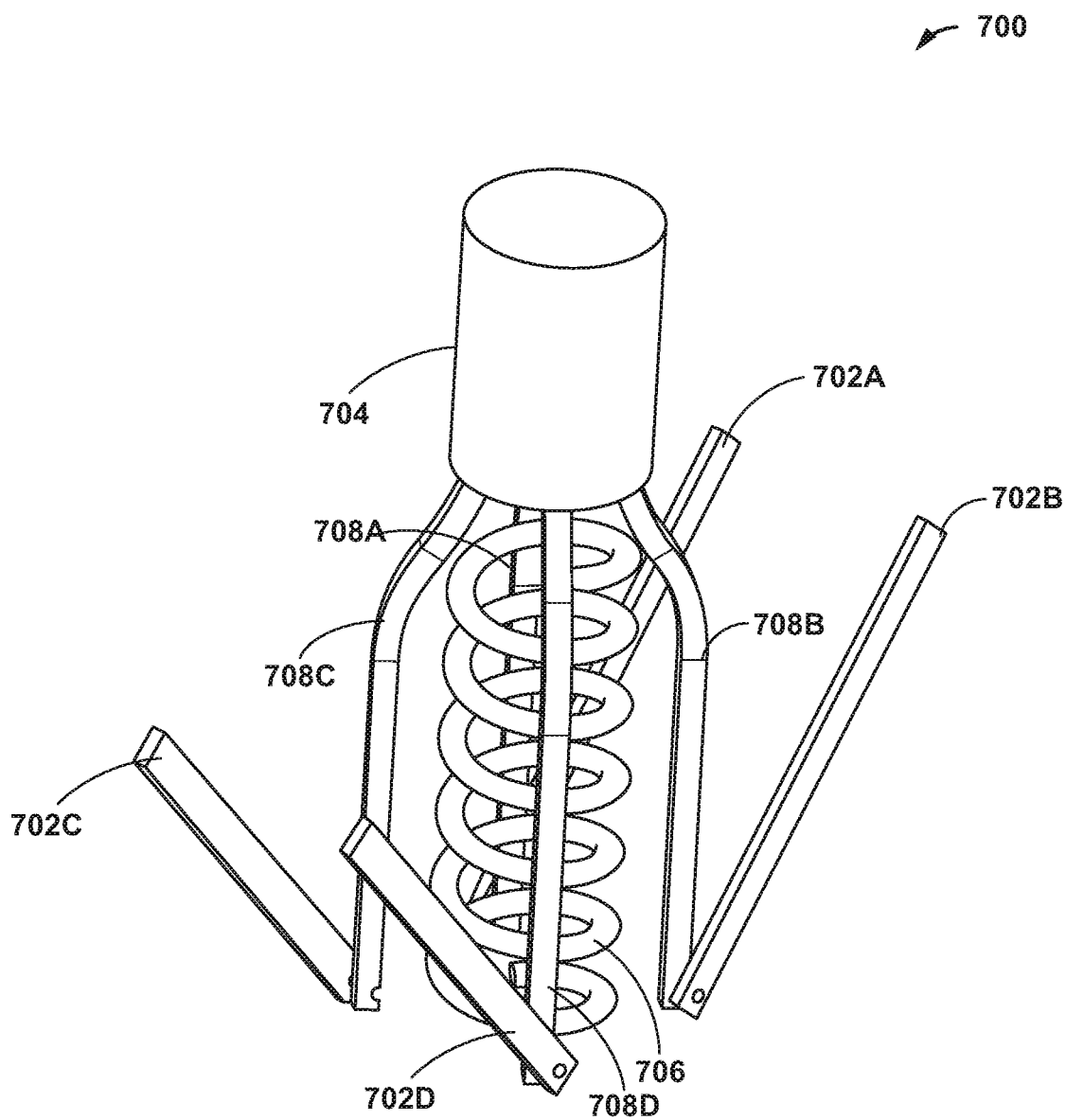
FIGS. 7A-7I are conceptual diagrams illustrating an example delivery system including four clamps extending from a distal end thereof and configured to deploy a helical coil to join tissues.
Figure 7C:
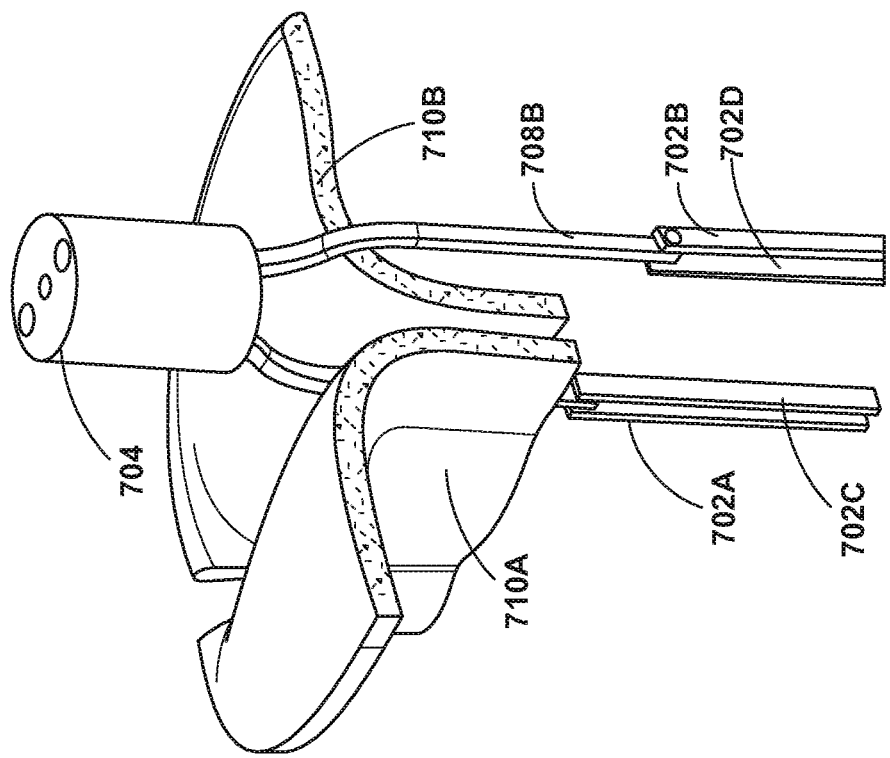
Figure 7B:
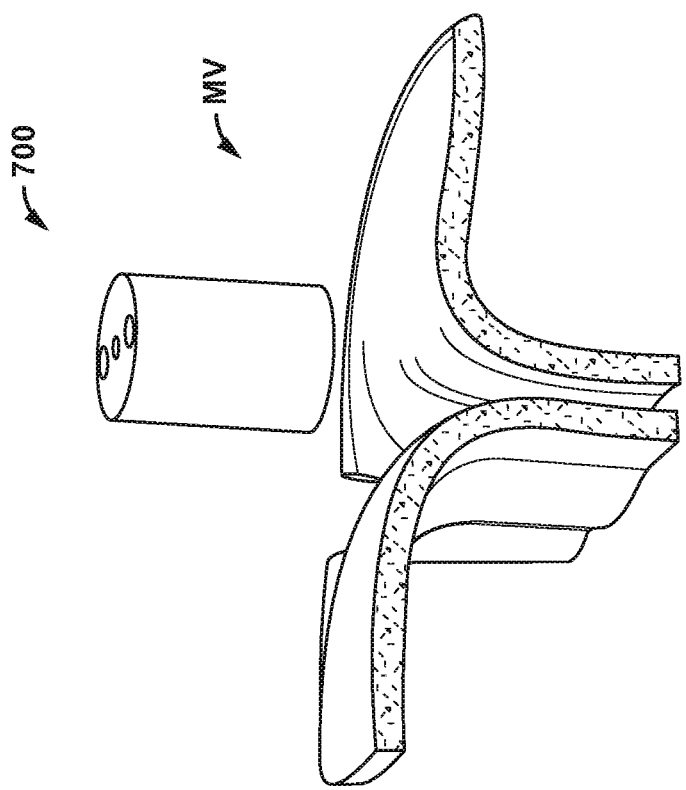

FIGS. 7B-7I illustrate an example method of delivering helical coil 706 to join edges of an anterior leaflet 710A and a posterior leaflet 710B of a mitral valve MV. As illustrated in FIG. 7B, a catheter of delivery system 700 may be introduced into the vasculature of a patient and steered to mitral valve MV. After positioning delivery system 700, clamps 702 and extension members 708 may be advanced from a distal end 704 of the catheter (and/or the catheter may be proximally retracted to expose clamps 702 and extension members 708) between anterior leaflet 710A and posterior leaflet 710B of mitral valve MV, as illustrated in FIG. 7C. As illustrated in FIG. 7C, delivery system 700 includes two extensions 708A and 708B, however, it is understood that delivery system 700 may include four extensions as illustrated in FIG. 7A.

Figure 7E:
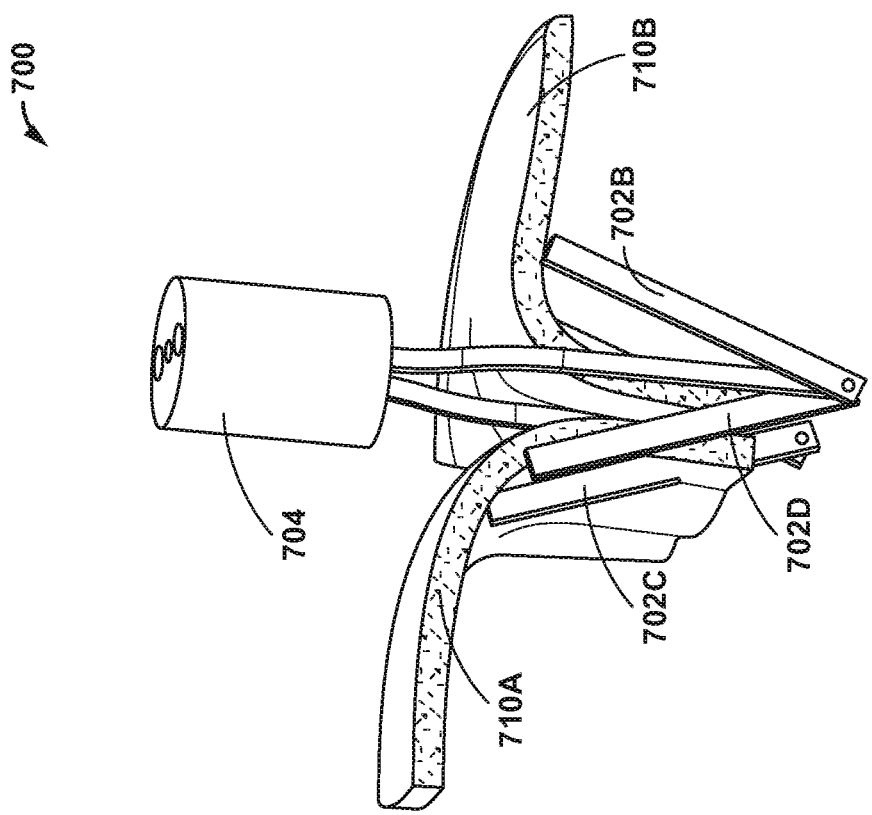
Figure 7D:
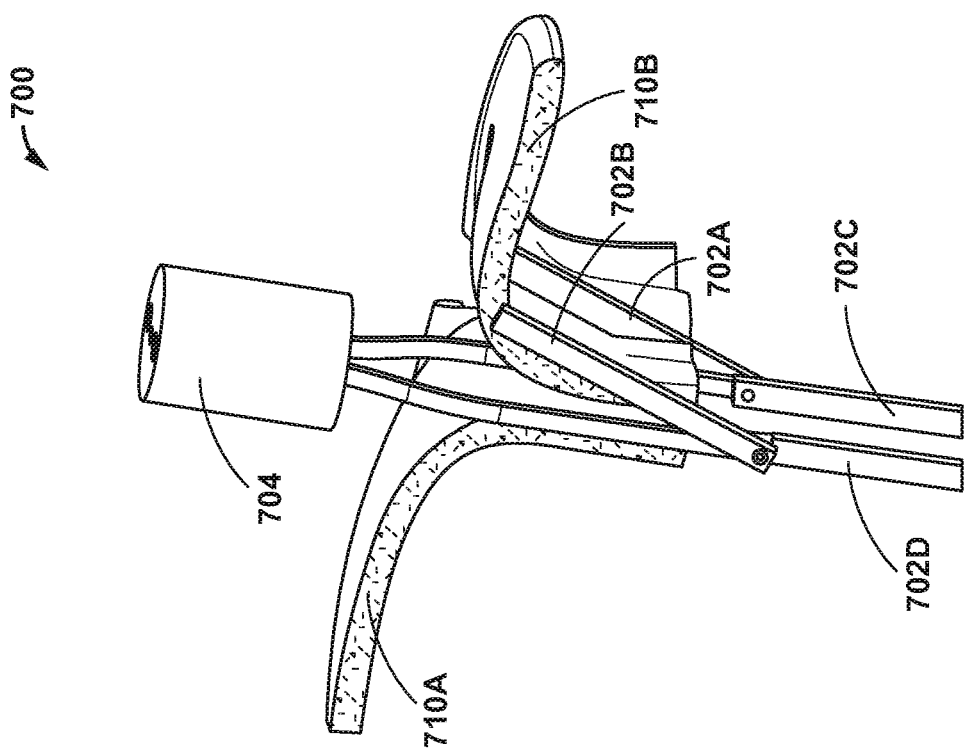

As illustrated in FIG. 7D, clamps 702A and 702B may be moved from an open configuration to a closed configuration to clamp posterior leaflet 710B. Clamps 702A and 702B may be actuated between the open and closed configuration using any suitable actuation mechanism. In some examples, extension members 708 may include one of the actuation members described above. As illustrated in FIG. 7E, clamps 702C and 702D may be actuated to clamp anterior leaflet 710A. By clamping anterior leaflet 710A and posterior leaflet 710B, delivery system 700 may reduce movement of mitral valve MV as helical coil 706 is advanced from distal end 704 of the catheter.

Figure 7G:
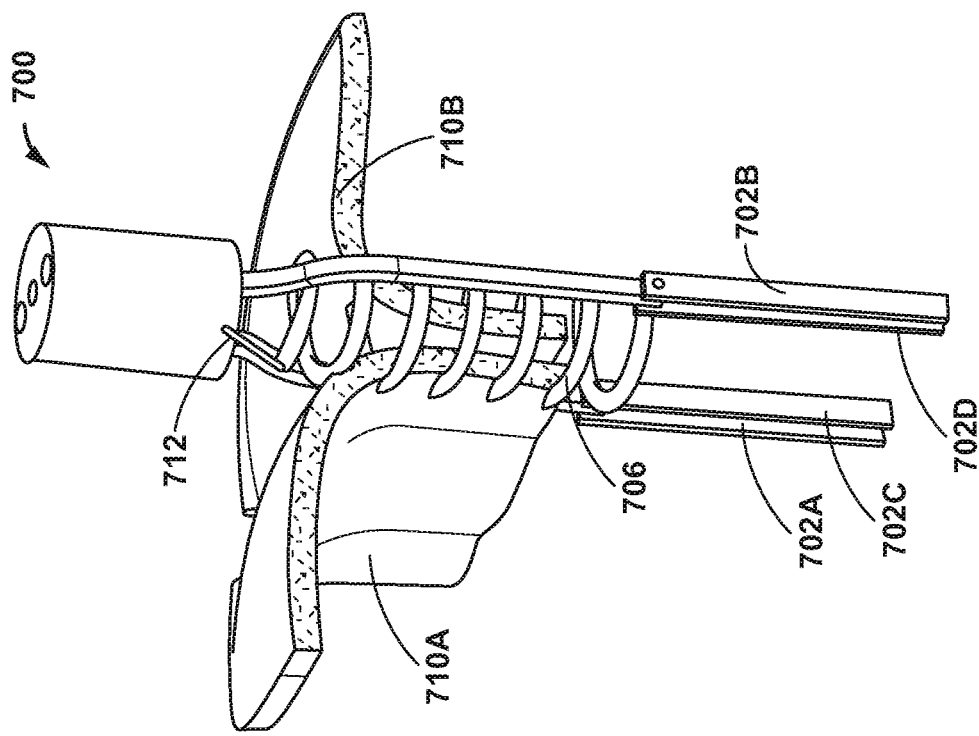
Figure 7F:
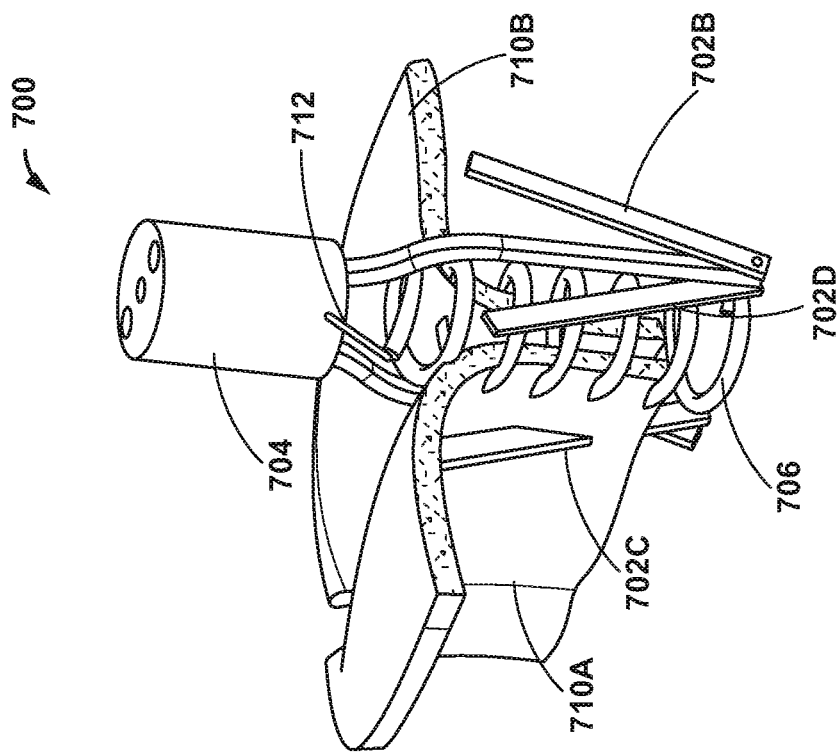

As illustrated in FIG. 7F, helical coil 706 may be advanced from distal end 704 to join a portion of anterior leaflet 710A to a portion of posterior leaflet 710B. For example, helical coil 706 may include a shape-memory alloy having a distal tip configured to penetrate tissue of mitral valve MV. Before deployment from distal end 704, helical coil 706 may be stretched to a straight configuration and held within a delivery catheter in a generally linear or at least a more linear configuration compared to a deployed coil 706. As helical coil 706 is advanced from distal end 704, helical coil may begin to regain a helix shape and penetrate tissue of the mitral valve. After helical coil 706 is deployed, clamps 702 may be opened to an open configuration, as illustrated in FIG. 7G.

Figure 7I:
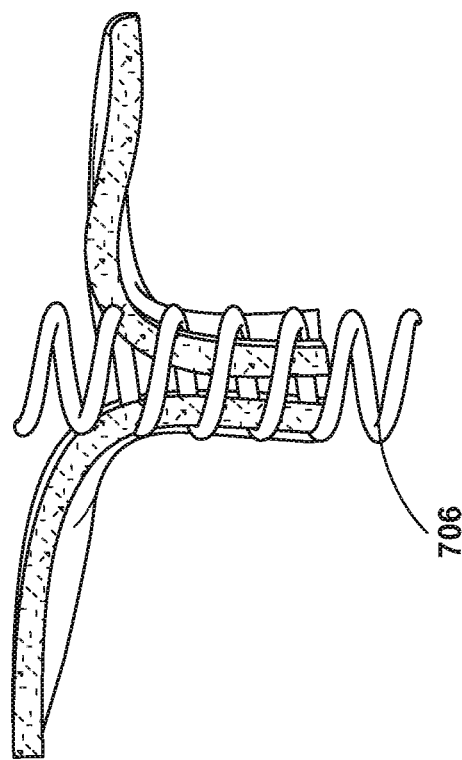
Figure 7H:
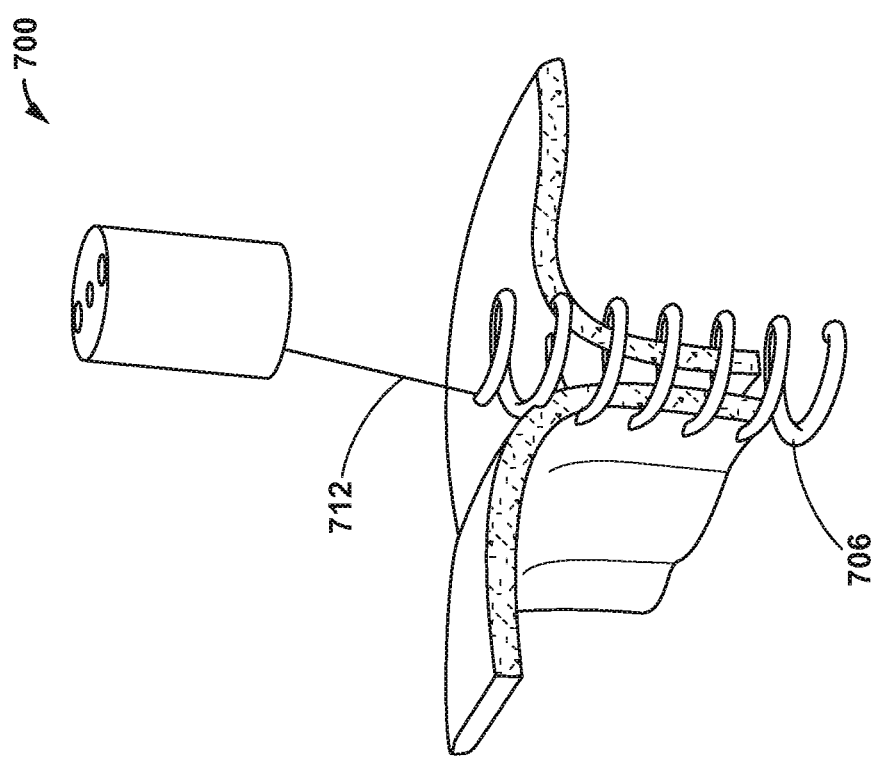

After the advancing helical coil 706 out distal end 704 and into tissue of mitral valve MV, clamps 702 may be withdrawn from mitral valve MV, as illustrated in FIG. 7H. Helical coil 706 may remain tethered to delivery system 700, e.g., distal end 704, by tether 712. Tether 712 may have a length selected to enable a clinician to assess movement of the mitral valve MV, e.g., movement of the mitral valve MV during beating of the heart, prior to release of tether 712 and withdrawal of delivery system 700. In some examples, if movement of the mitral valve MV is not satisfactory, then helical coil 706 may be retracted using tether 712 and redeployed, or a second helical coil may be implanted. When the user desires to release the implant coil, the tether is retracted, and the catheter is removed, as illustrated in FIG. 7I.

Although helical coil 706 is illustrated in FIGS. 7A-7I as being implanted in a superior-inferior direction (e.g., "vertically"), in other examples, a coil may be implanted medial laterally (e.g., "horizontally"). FIGS. 8A-8C are conceptual diagrams illustrating an example delivery system 800 including a catheter 801, clamps 802A and 802B, and a coil 806. FIG. 8A is a view down the longitudinal axis of catheter 801, FIG. 8B is a side view showing the clamp 802A, and FIG. 8C is another side view showing both clamps 802A, 802B in a closed configuration, as well as the end of coil 806. Coil 806 is configured to be implanted into tissue in a lateral direction, e.g., relative to a longitudinal axis of catheter 801. To enable a medial lateral implant delivery of coil 806, clamps 802A and 802 B may be configured to support a longer segment of leaflet (compared to clamps used to deliver a coil intended to be implanted in a superior-inferior direction). For example, clamps 802A and 802 B may have an L-shape.

Additionally, or alternatively, two separate clamping catheters may be used to implant a coil medial laterally. FIGS. 9A-9C are conceptual diagrams illustrating an example delivery system 900 including a first catheter 901A having two clamps 902A and 902C and configured to deliver a coil 906, and a second catheter 901B having two clamps 902C and 902D. FIG. 9A is a view down the longitudinal axis of catheters 901A, 901B, FIG. 9B is a side view showing the clamps 902A, 902C, and FIG. 9C is another side view showing both clamps 902A, 902C in a closed configuration, as well as the end of coil 906.

In some examples, first catheter 901A and second catheter 901B may include a bifurcated catheter, e.g., a catheter having a distal portion that bifurcates in the medial lateral direction. In other examples, catheters 901A, 901B may be physically separate from each other along their respective entire longitudinal lengths. Coil 906 is configured to be implanted into tissue in a lateral direction, e.g., relative to a longitudinal axis of catheter 901A. To enable a medial lateral implant delivery of coil 906, clamps 902A and 902B may be deployed from first catheter 901A and clamps 902C and 902D may be deployed from second catheter 901B. Clamps 902A-902D may be configured to support a longer segment of leaflet. In this way, delivery system 900 may provide support to deploy coil 906 medial laterally.

Additionally, or alternatively, in examples in which a coil is implanted medial laterally, two shorter implant coils could be deployed towards each other from a bifurcated catheter. FIGS. 10A-10C are conceptual diagrams illustrating an example delivery system 1000 including a first catheter 1001A including two clamps 1002A and 1002B, and configured to deliver a first coil 1006A, and a second catheter 1001B including two clamps 1002C and 1002D, and configured to deliver a second coil 1006B. FIG. 10A is a view down the longitudinal axis of catheters 1001A, 1001B, FIG. 10B is a side view showing the clamps 1002A, 1002C, and FIG. 10C is another side view showing both clamps 1002A, 1002C in a closed configuration, as well as the end of coil 1006.

In some examples, first catheter 1001A and second catheter 1001B may include a bifurcated catheter. In other examples, catheters 1001A, 10B may be physically separate from each other along their respective entire longitudinal lengths. To enable a medial lateral implant delivery of first coil 1006A and second coil 1006B, clamps 1002A and 1002B may be deployed from first catheter 1001A and clamps 1002C and 1002D may be deployed from second catheter 1001B. Clamps 1002A-1002D may be configured to support a longer segment of leaflet. First coil 1006A and second coil 1006B may be advanced simultaneously or independently from respective first catheter 1001A and second catheter 1001B. In this way, delivery system 1000 may provide support to deploy coils 1106A and 1006B medial laterally.

Figure 11A:
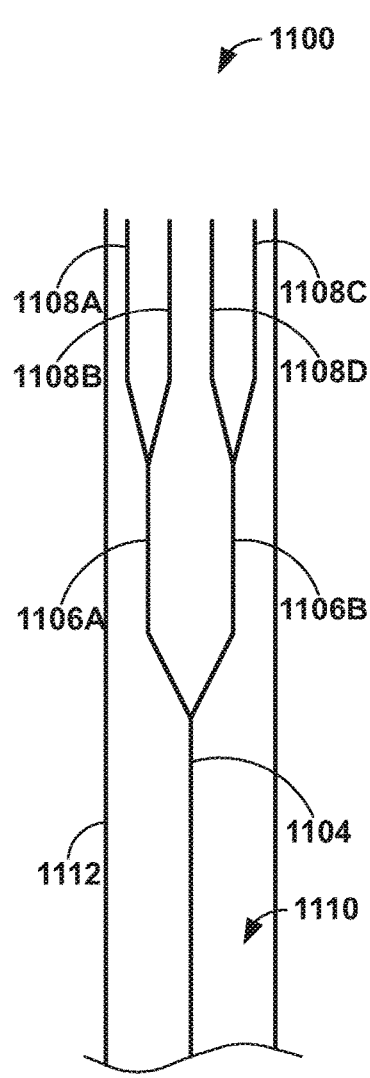
FIGS. 11A-11E are conceptual diagrams illustrating an example delivery device that includes deployable branched paddles.
Figure 11B:
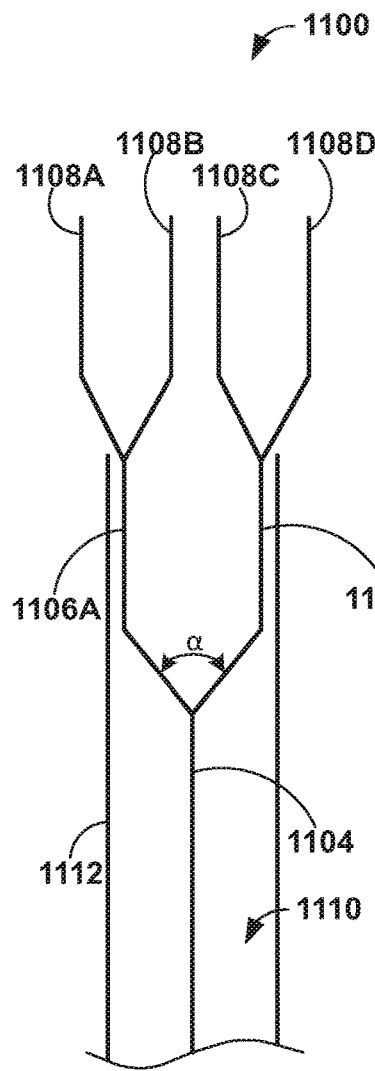

In some examples, a delivery device may include structures formed from a shape-memory material, referred to herein as shape-memory structures. The shape memory structure can be configured to engage tissue upon deployment from a catheter. FIGS. 11A-11E are conceptual diagrams illustrating an example delivery device 1100 including an elongate member 1102 extending from a common member 1104, to intermediate branches 1106A and 1106B, to branched paddles 1108A-1108D. Elongate member 1102 may be formed at least partially from include a shape-memory alloy, such as a nickel titanium alloy. For example, elongate member 1102, e.g., paddles 1108A-1108D, may have a preformed shape configured to engage and "grab" leaflets of a valve of a heart upon deployment. As illustrated in FIG. 11A, elongate member 1102, e.g., paddles 1108A-1108D, are configured to be held in a "collapsed" configuration when inside a lumen 1110 of a catheter 1112. As illustrated in FIG. 11B, paddles 1108A-1108D are configured to self-expand and may begin to move toward the preformed shape as paddles 1108A-1108D are advanced out of lumen 1104 and/or as catheter 1112 is retracted away from elongate member 1102. In other examples, in addition to or instead of self-expanding, an expandable element, such as a balloon, may be used to move intermediate branches 1106A and 1106B away from each other and/or to move paddles 1108A, 1108B away from each other and/or to move paddles 1108C, 1108D away from each other.

Figure 11C:
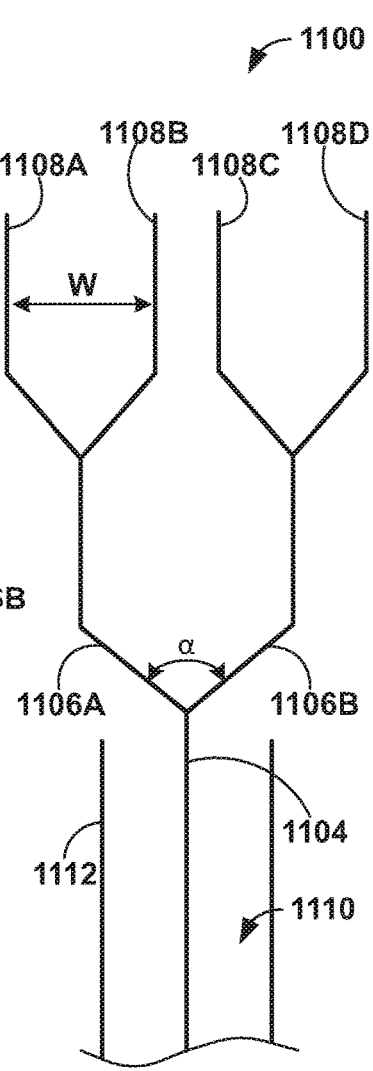

In some examples, a length and/or preformed shape of intermediate branches 1106A and 1106B may control a width "W" of paddles 1108A-1108D in a fully open configuration, as illustrated in FIG. 11C. For example, width "W" may be based on how far intermediate branches 1106A and 1106B are advanced out of lumen 1110, and thus how wide of an opening angle intermediate branches 1106A and 1106B are allowed to achieve.

Once the paddles 1108A-1108D are advanced out of lumen 1104 are at a target position with respect to the valve leaflets, common member 1104 may be pulled back into lumen 1110, which results in pulling the intermediate branches 1106A and 1106B toward catheter 1112 and decreasing the angle α between intermediate branches 1106A and 1106B and bringing paddles 1108A-1108D back together (e.g., as shown in FIG. 11A), trapping the captured leaflets between paddles 1108A-1108D.

Figure 11E:
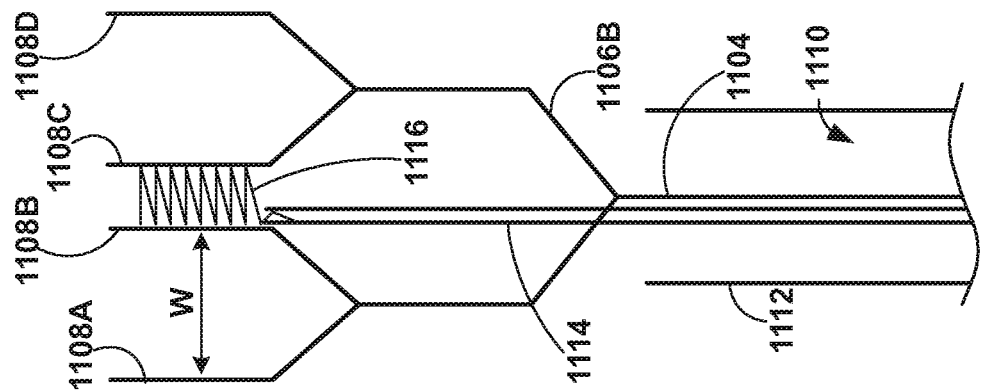
Figure 11D:
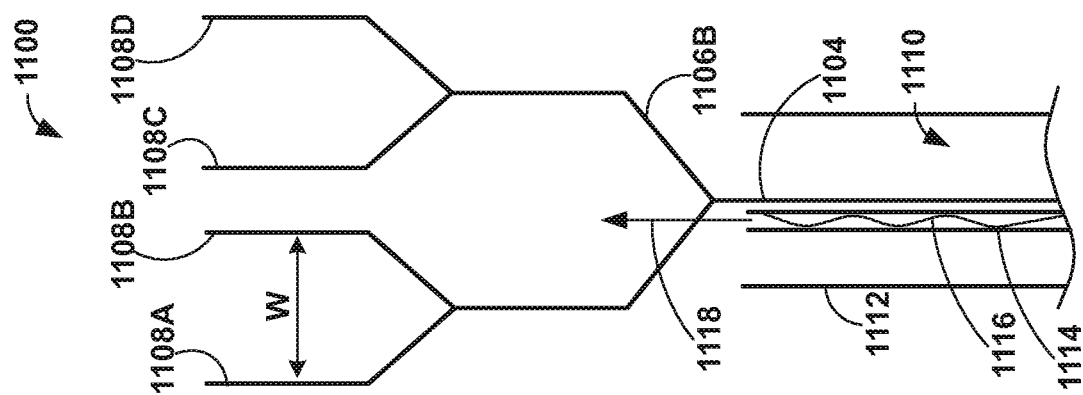

In some examples, catching the leaflets may be assisted by relatively small barb-like structures, other types of surface protrusions, or the like along the surfaces of paddles 1108A-1108D intended to contact the leaflets (e.g., along the surfaces of paddles 1108A, 1108B facing each other and the surfaces of paddles 1008C, 1008D facing each other). In some examples, delivery device 1100 may be used to delivery an IMD, for example, as described above in reference to FIGS. 7A-10C. For example, as illustrated in FIG. 11D, a second catheter 1114 having a coil member 1116 may be advanced from catheter 1112 between intermediate branches 1106A and 1106B (e.g., in the direction of arrow 1118). As illustrated in FIG. 11E, coil 1116 may be advanced out of second catheter 1114 to penetrate and suture tissue of leaflets captured by paddles 1108A-1108D.

Figure 12:
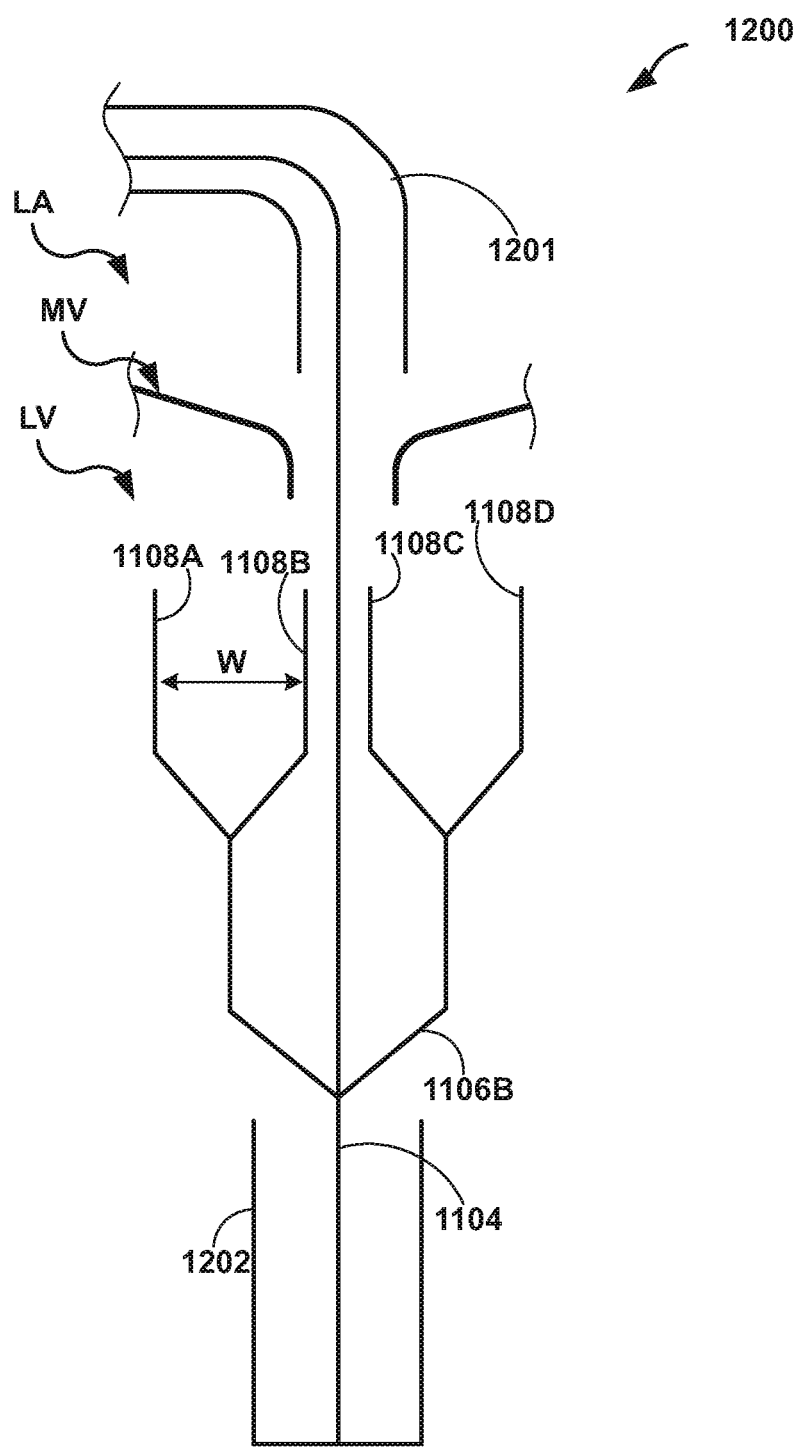
FIG. 12 is a conceptual diagram illustrating a delivery device including catheter including a capsule configured to deploy the elongate member illustrated in FIGS. 11A-11C.

Delivery device 1100 may be delivered to the target valve being repaired using any suitable technique, such as a transcatheter technique. For example, delivery device 1100 may be deployed through the left ventricle or transeptally (e.g., through the left atrium). In examples in which delivery device 1110 is deployed transeptally, elongate member 1102 may be housed in a capsule. FIG. 12 is a conceptual diagram illustrating an example delivery device 1200 including a catheter 1201 and a capsule 1202 configured to deploy elongate member 1110. For example, capsule 1202 may be advanced from left atrium LA through mitral valve MV to left ventricle LV. Then, as illustrated in FIG. 12, capsule 1202 may be opened to expose paddles 1108A-1108D.

Figure 13B:
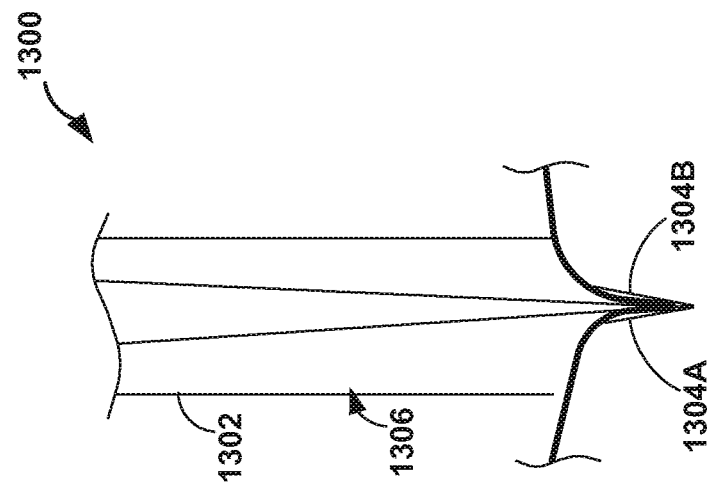
FIGS. 13A and 13B are conceptual diagrams illustrating an example delivery device including clamps configured to engage leaflets of mitral valve upon deployment from a catheter.
Figure 13A:
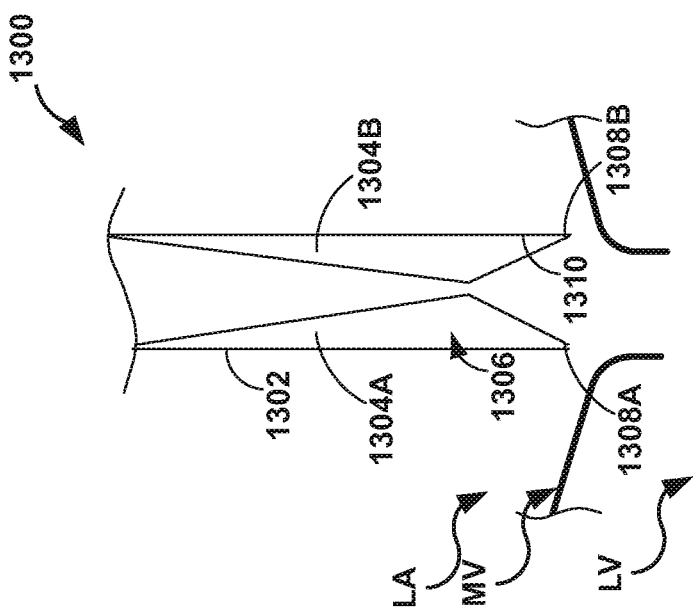

In some examples, clamps may be formed from a shape memory material and may be configured to engage and "grab" leaflets of mitral valve MV upon deployment from a catheter. FIGS. 13A and 13B are conceptual diagrams illustrating an example delivery device 1300 including clamps 1304A and 1304B configured to engage leaflets of mitral valve MV upon deployment from a catheter 1302. For example, clamps 1304A and 1304B may be held in a collapsed configuration (also referred to herein as a delivery configuration) when inside lumen 1306 of catheter 1302. Clamps 1304A, 1304B may be configured to be biased to a preformed shape, such that when in lumen 1306, ends 1308A and 1308B of clamps 1304A and 1304B engage interior wall 1310 of catheter 1302. After deployment of distal ends 1308A and 1308B from lumen 1306, clamps 1304A and 1304B may be configured to self-move to the preformed shape configured to engage leaflets of mitral valve MV. The preformed shape, which may correspond to a closed clamp configuration, is shown in FIG. 13B.

Figure 14A:
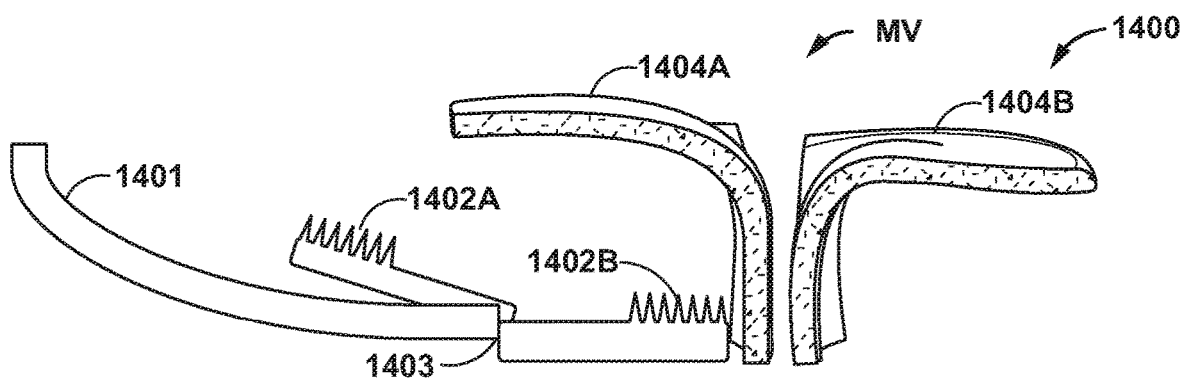
FIGS. 14A-14C are conceptual diagrams illustrating an aortic approach of a delivery device configured to clamp mitral valve leaflets.
Figure 14B:
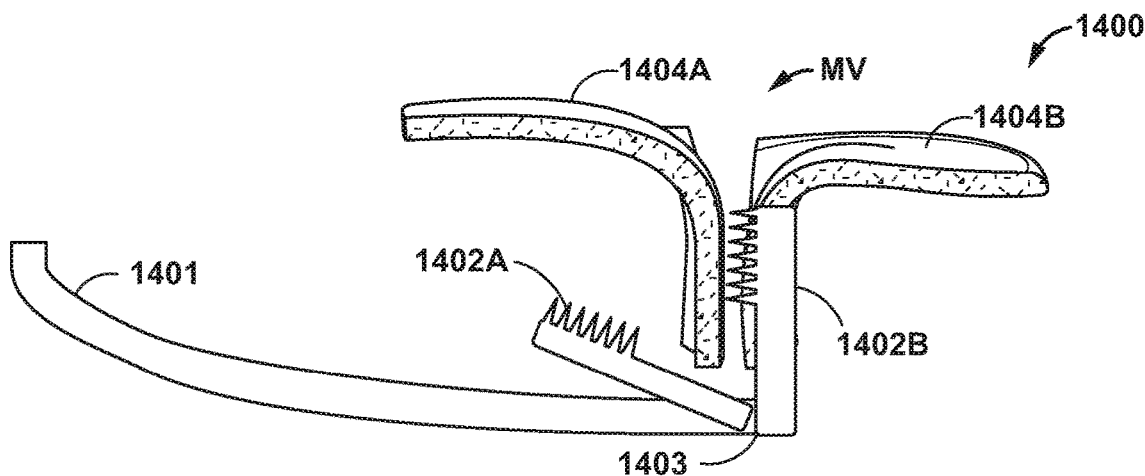
Figure 14C:
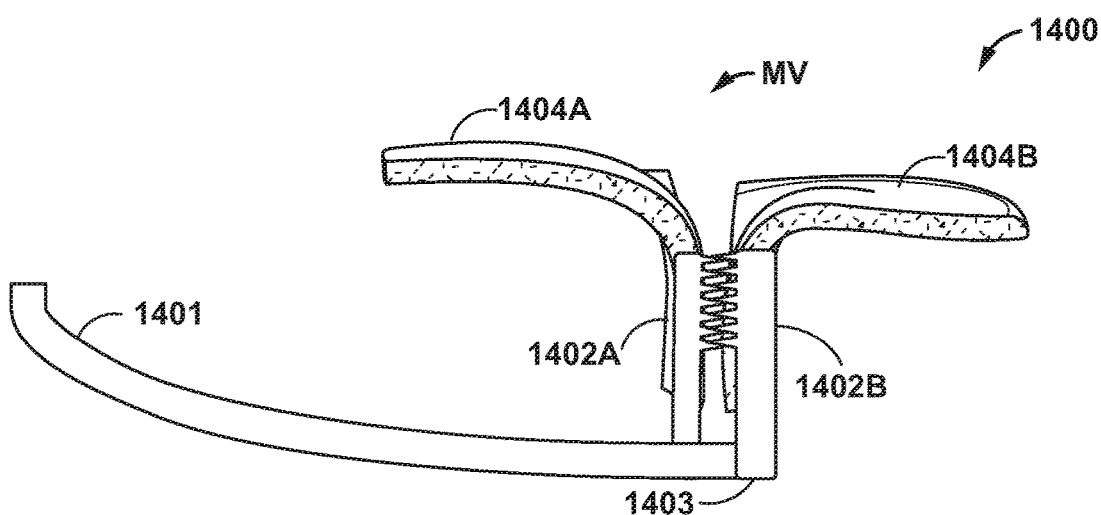

FIGS. 14A-14C are conceptual diagrams illustrating an aortic approach of a delivery device 1400 configured to clamp mitral valve MV leaflets. The aortic approach may include steering catheter 1401 through the aorta of the patient into the left ventricle LV. In some examples, the aortic approach may not require puncturing the septal wall and may be a faster deployment due to catheter 1401 naturally steering towards mitral valve MV when delivered via the aorta. After steering the catheter to the left ventricle LV, clamps 1402A and 1402B may be advanced from a distal end 1403 of catheter 1401. In some examples, a pre-shaped distal end (not shown) of catheter 1401 could abruptly hook catheter 1401 into anterior leaflet 1404A.

In some examples, a clinician may actuate clamp 1402B to a closed configuration, e.g., as describe above, to capture posterior leaflet 1404B of mitral valve MV. In other examples, clamps 1402A, 1402B may be biased to the closed configuration (e.g., due to a spring or due to shape memory structures) and may automatically capture posterior leaflet 1404B once released from a distal end of catheter 1401 and if positioned proximate posterior leaflet 1404B. In some examples, catheter 1401 may be controlled to bring posterior leaflet 1404B in contact with anterior leaflet 1404A. The clinician may actuate clamp 1402A, e.g., as describes above, to capture anterior leaflet 1404A of mitral valve MV, or clamp 1402B may automatically move to the closed position to capture anterior leaflet 1404A. In some examples, clamp 1402A may capture anterior leaflet 1404A before clamp 1404B is controlled to capture posterior leaflet 1404B. In some examples, capturing posterior leaflet 1404B before anterior leaflet 1404A may be easier because pulling catheter 1401 may be easier than pushing catheter 1401 due to backlash in catheter 1401.

As discussed above, any suitable medical device may be used to attach the leaflets of a mitral valve together, e.g., to form an end to end repair of the mitral valve. The medical device can be referred to as a closure device and can be, for example, a helical coil, a bridge, a U-clip, a multi-clamp device, sutures, or any other suitable device. Example closure devices are described with reference to FIGS. 15A-23.

Figure 15A:
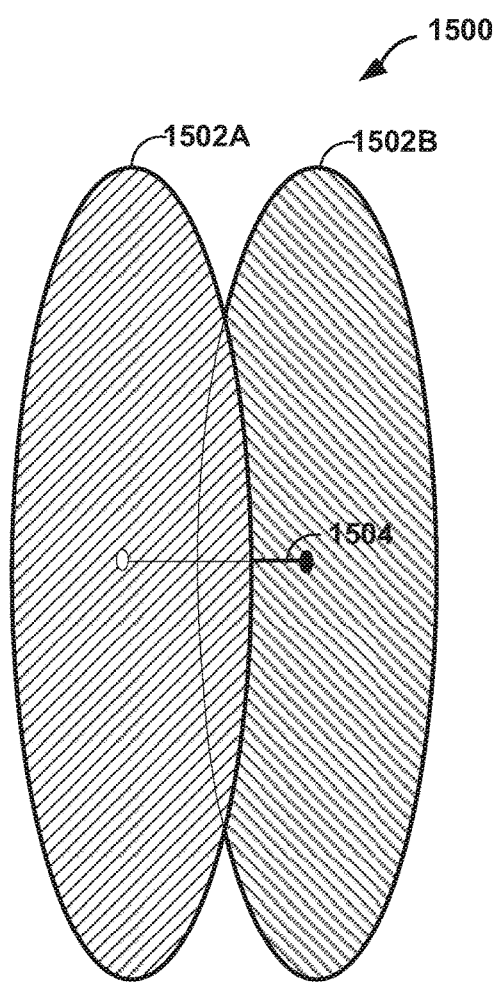
FIGS. 15A and 15B are conceptual diagrams illustrating an example closure device configured to clamp mitral valve leaflets.
Figure 15B:
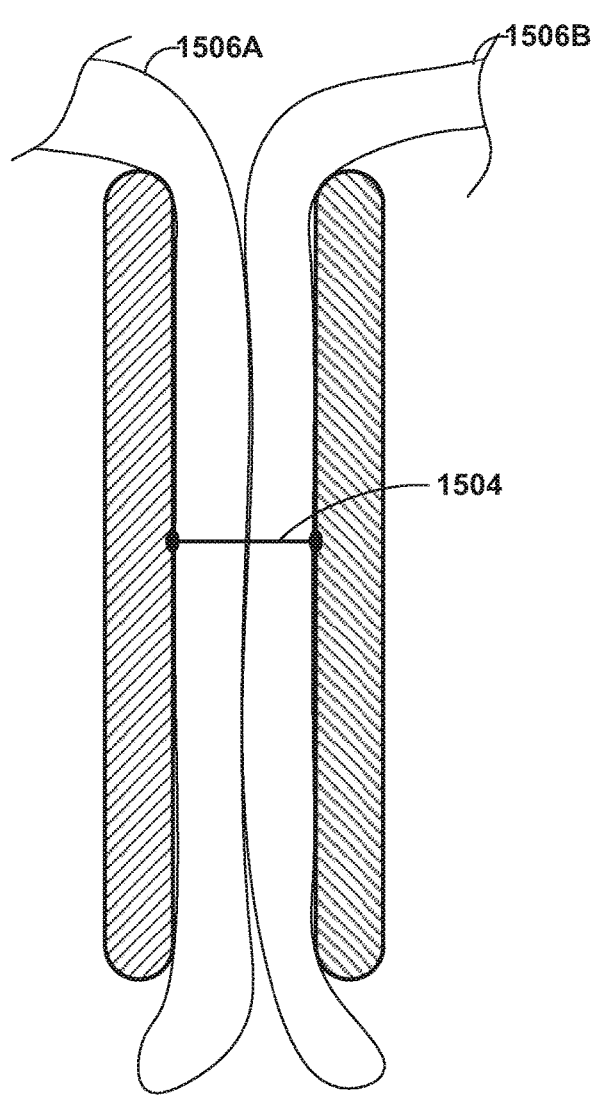

FIGS. 15A and 15B are conceptual diagrams illustrating another example closure device 1500 configured to clamp mitral valve MV leaflets. Closure device 1500 includes two pads 1502A and 1502B held together under tension via a connecting tether 1504. Pads 1502A and 1502B are configured to sandwich anterior leaflet 1506A and posterior leaflet 1506B. In some examples, pads 1502A and 1502B may not create a seal, but rather grip and hold together anterior leaflet 1506A and posterior leaflet 1506B. In some examples, a transaortic approach enables puncturing of the anterior leaflet 1506A and posterior leaflet 1506B in distinct, successive steps. The clamping methods described earlier may be incorporated to facilitate accurate puncturing of anterior leaflet 1506A and/or posterior leaflet 1506B. A transseptal approach may also be considered, in which closure device 1500 may be delivered initially as two physically separate pads 1502A, 1502B that may be drawn together via one of the earlier described devices or techniques, and locked, prior to final release.

Figure 16C:
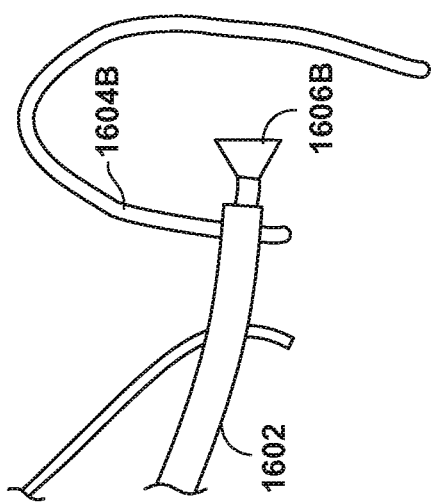
FIGS. 16A-16F are conceptual diagrams illustrating an example method of implanting the closure device illustrated in FIG. 15A using an aortic approach.
Figure 16B:
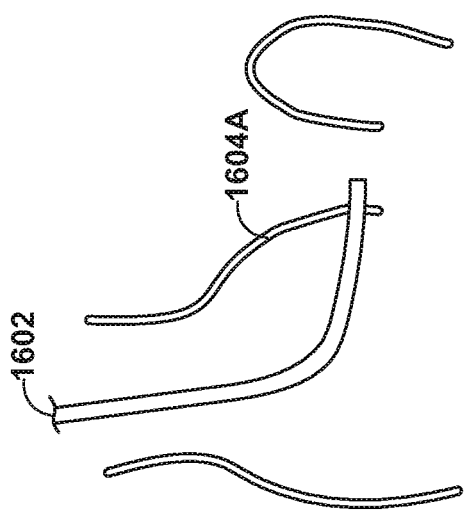
Figure 16A:
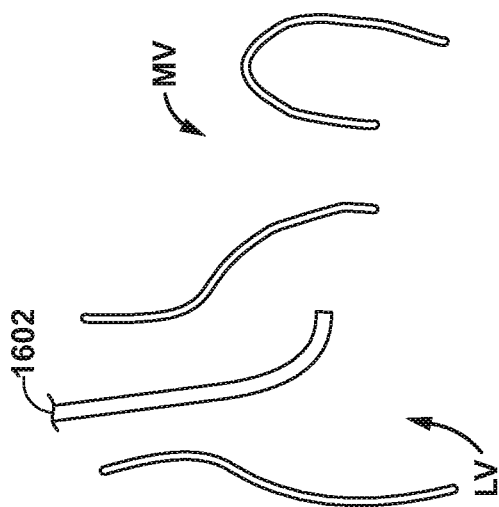
Figure 16F:
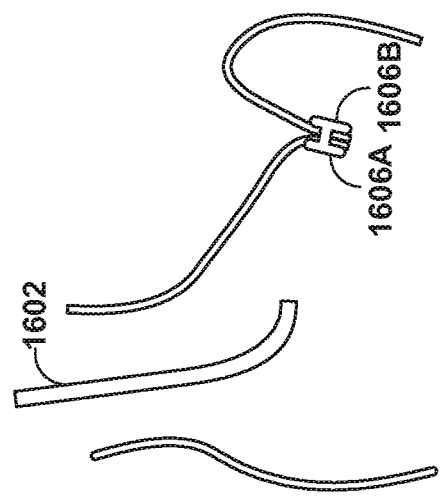
Figure 16E:
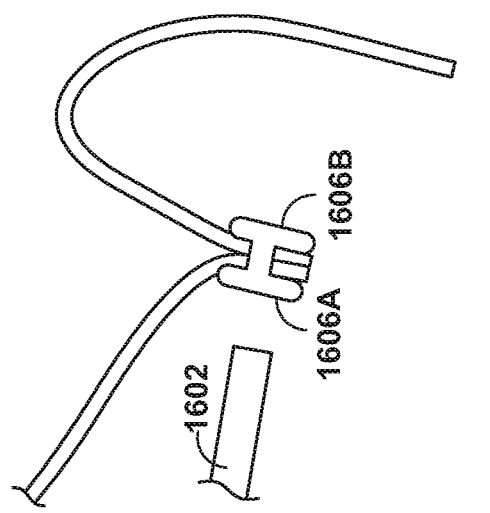
Figure 16D:
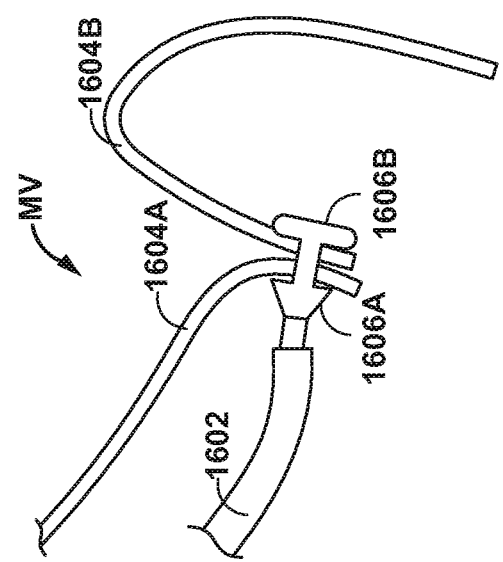

FIGS. 16A-16F are conceptual diagrams illustrating an example method of implanting closure device 1500 using an aortic approach. As illustrated in FIG. 16A, catheter 1602 is steered through the vasculature of a patient to the aorta, and from the aorta into the left ventricle LV near the mitral valve MV. As illustrated in FIG. 16B, catheter 1602 is used to cross (e.g., puncture) anterior leaflet 1604A. As illustrated in FIG. 16C, catheter 1602 is used to cross (e.g., puncture) posterior leaflet 1604B. After crossing posterior leaflet 1604B, catheter 1602 may be controlled to expose posterior pad 1606B. Then, catheter 1602 may be retracted through anterior leaflet 1604A and posterior leaflet 1064B of mitral valve MV. After retracting catheter 1602, catheter 1602 may be controlled to expose anterior pad 1608A on the other side of anterior leaflet 1604A from posterior leaflet 1604B, as illustrated in FIG. 16D. After exposing anterior pad 1608A, catheter 1602 may be controlled to release anterior pad 1608A, as illustrated in FIG. 16E, at which point closure device 1500 may be fully release from catheter 1602. In other examples, if another mechanism is used to connect closure device 1500 to catheter 1602, this mechanism may be actuated or otherwise modified to disengage (e.g., decouple) closure device 1500 from catheter 1602. As illustrated in FIG. 16F, after closure device 1500 is disengaged from catheter 1602, catheter 1602 may be withdrawn from the vasculature of the patient.

Figure 17A:
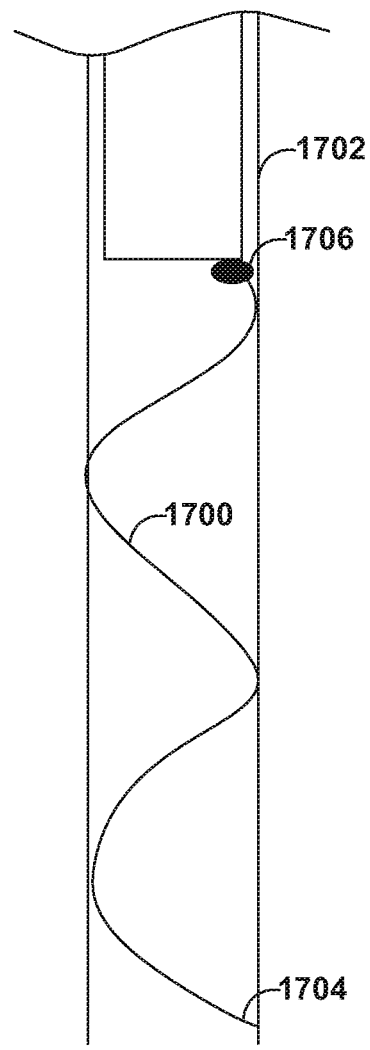
FIGS. 17A and 17B are conceptual diagrams illustrating an example medical device including a helical coil configured to join tissues.
Figure 17B:
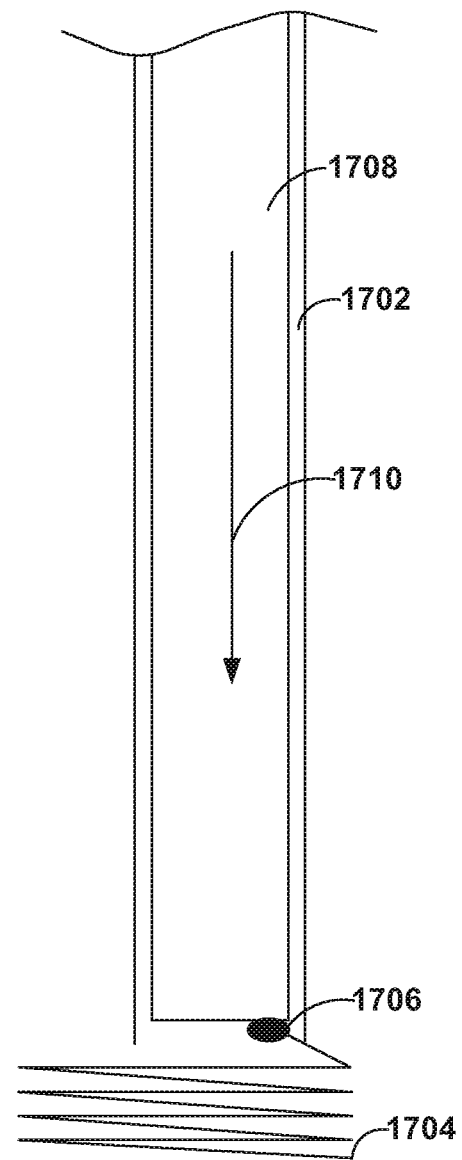

FIGS. 17A and 17B are conceptual diagrams illustrating an example medical device 1700 including a helical coil configured to join tissue, e.g., leaflets of a heart valve. medical device 1700 may include a coil that is heat set in a coil shape. To reduce the profile of delivery system 1702, medical device 1700 may be housing in delivery system 1702 in a substantially straight configuration (e.g., a deformed configuration) or at least a more straight configuration compared to the deployed configuration. Upon advancing medical device 1700 from delivery system 1702, e.g., by moving push wire 1708 as indicated by arrow 1710, medical device 1700 may return to a coiled configuration (e.g., a preformed shape). In some examples, medical device 1700 may include an incisive distal tip 1704 configured to penetrate tissue. In some examples, as medical device 1700 it advanced from delivery system 1702, medical device 1700 may penetrate and twirl through tissue. In some examples, a proximal end of d 1700 may include a tissue stopper disk 1706, e.g., similar to a tissue stopper disk of a u-clip.

Figure 18B:
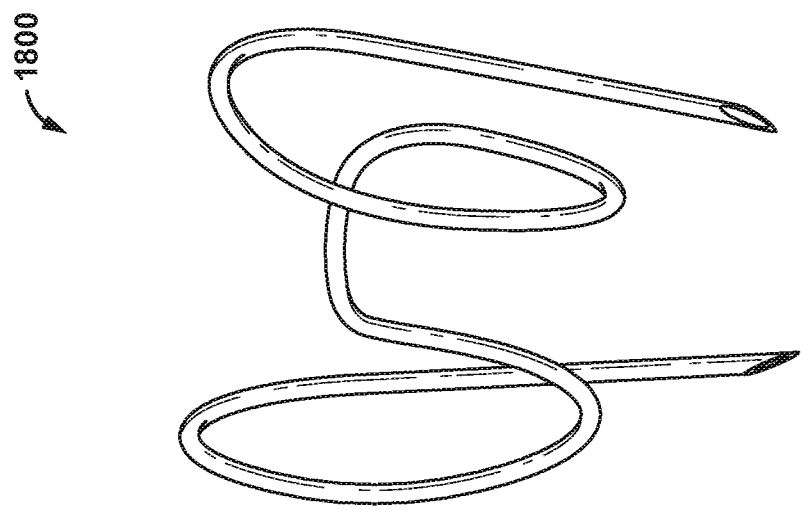
FIGS. 18A and 18B are conceptual diagrams illustrating an example bridge clip.
Figure 18A:
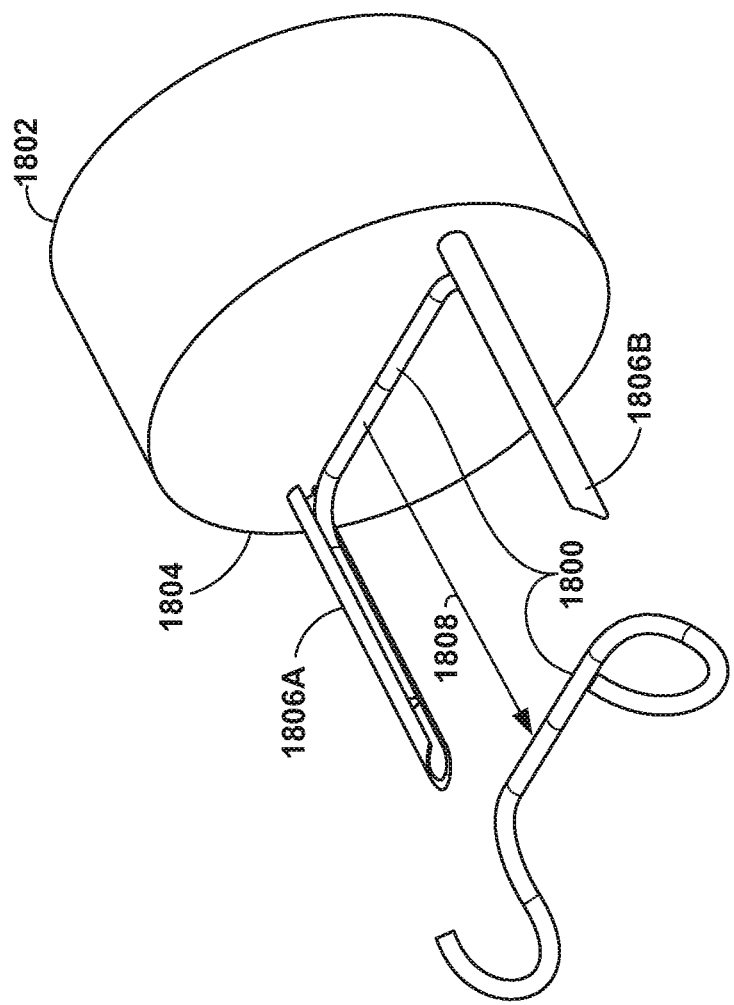

FIG. 18A is a conceptual diagram illustrating an example bridge clip 1800 and FIG. 18B is a photograph of an example bridge clip 1800. Bridge clip 1800 may be used in place of, or in addition to any of the coils discussed above. Bridge clip 1800 may be formed at least partially from shape-memory material. In some examples, bridge clip 1800 is deployable in the direction of arrow 1808 from a distal end 1804 of a catheter 1802. In some examples, needles 1806A and 1806B may extend from distal end 1804 of catheter 1802. Needles 1806A and 1806B may be configured to penetrate through tissue, e.g., the tissue of the posterior leaflet and/or anterior leaflet to position bridge clip 1800. Thereafter, bridge clip 1800 may be deployed by retracting needles 1806A and 1806B into catheter 1802 such that bridge clip 1800 allowed to flex into a preformed shape. The posterior leaflet and/or anterior leaflet may be drawn together or held in place by bridge clip 1800. In some examples, multiple bridge clips 1800 may be deployed, either through a parallel set of needles or in series through the same needles in a cartridge mechanism. After release of bridge clip 1800, a tether could remain attached to the top of bridge clip 1800, allowing for retrieval and, in some cases, repositioning, after assessing movement of mitral valve MV.

Figure 19:
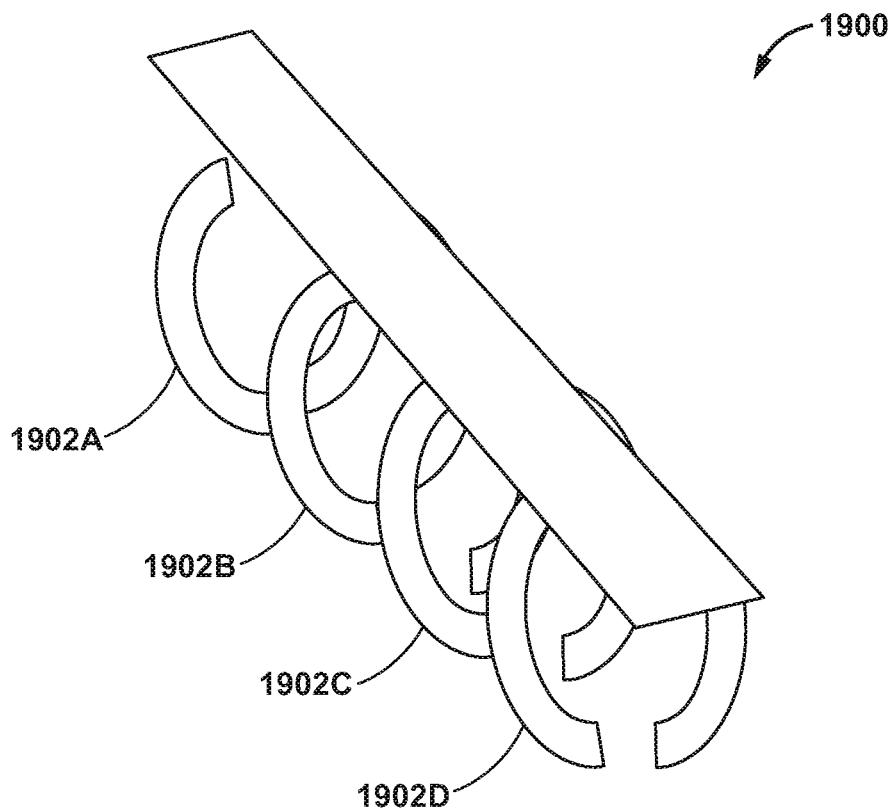
FIG. 19 is a conceptual diagram illustrating an example bridge clip including multiple legs.

In some examples, a bridge clip may include multiple legs on a single bridge. FIG. 19 is a conceptual diagram illustrating an example bridge clip 1900 including multiple legs 1902A-1902D. By using multiple legs, bridge clip 1900 may provide a wider edge to edge repair compared to a bridge clip with only two legs.

Figure 20:
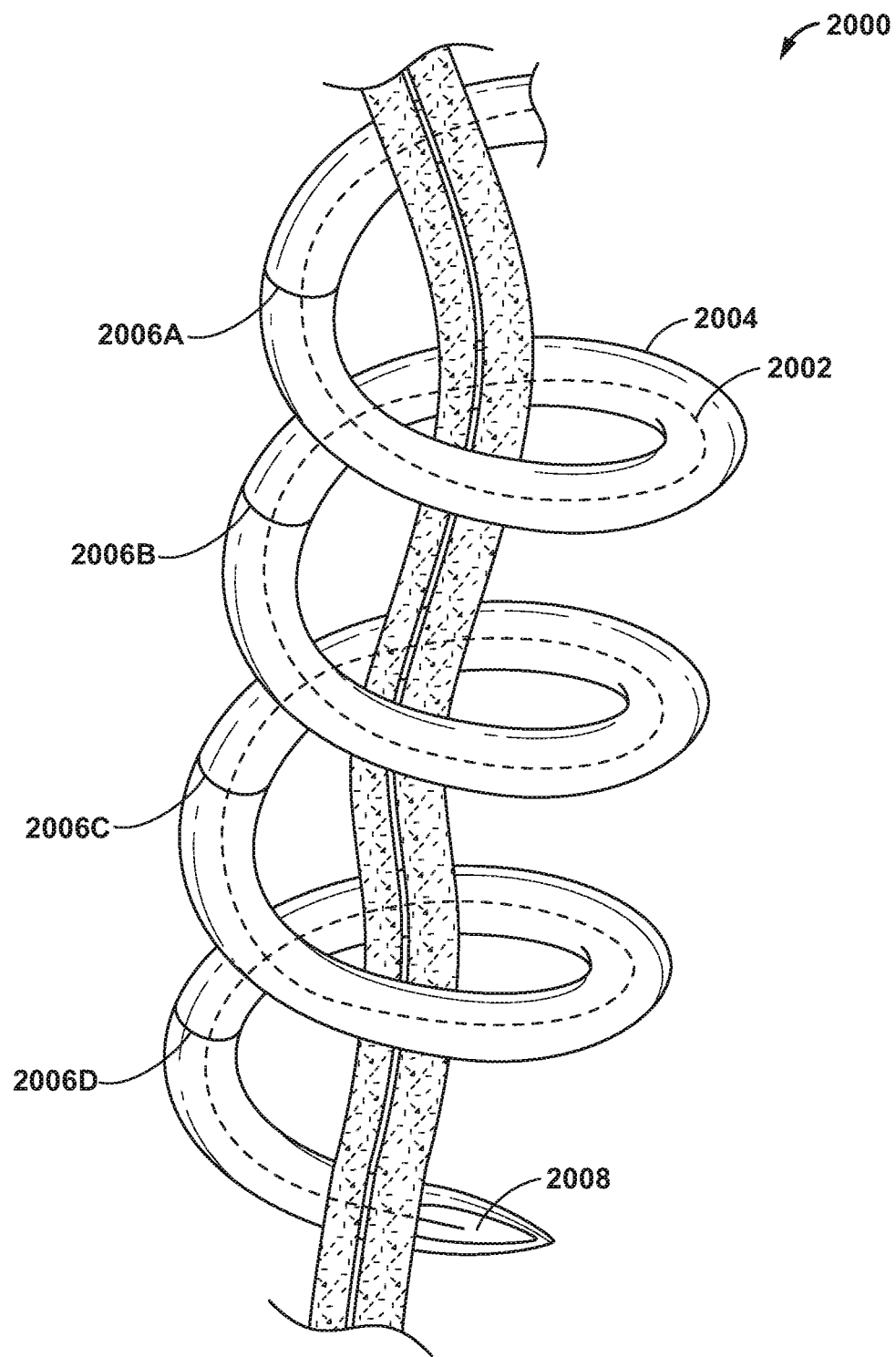
FIG. 20 is a conceptual diagram illustrating an example delivery device including a suture along a helical needle.

In some examples, a helical coil may be used to deliver a suture, which acts as a closure mechanism for attaching two leaflets of a heart valve together. FIG. 20 is a conceptual diagram illustrating an example suture delivery device 2000 including a suture 2002 along a helical needle 2004. Helical needle 2004 is relatively rigid and configured to penetrate through tissue, e.g., through the leaflets of a valve, and may be formed from any suitable medical grade material, such as, for example, a nickel titanium alloy, stainless steel, or the like.

Suture 2002 may extend along an outside diameter (OD) of helical coil in some examples, or along an inner diameter in other examples. In some examples, delivery device 2000 may include with periodic loop restraints 2006A-2006D. Periodic loop restraints 2006A-2006D may keep suture 2002 closely running along the OD (or inner diameter) of helical needle 2004, e.g., even as helical needle 2004 is advanced/ rotated through tissue. Suture 2002 may be attached to needle 2004 using any suitable technique, such as via a knot or crimped down via pledget 2008 (or another suitable structure), which sits at the tip of helical needle 2004. In this way, when helical needle 2004 is rotated forward (into tissue), suture 2002 stays taut and in motion with helical needle 2004. When helical needle 2004 is reversed/retracted, pledget 2008 butts up against the penetrated leaflet tissue and allows helical needle 2004 to be retracted while suture 2002 remains in place. A suture 2002 maybe implanted in this way in either a medial-lateral direction or a superior-inferior direction.

Figure 21A:
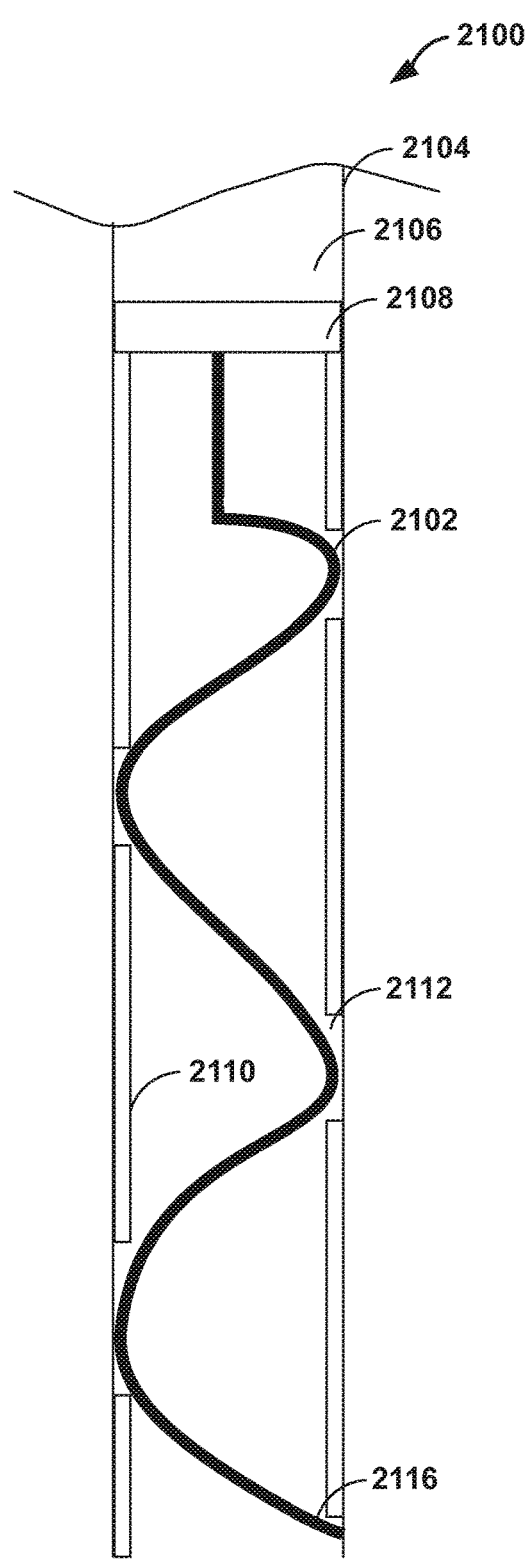
FIGS. 21A and 21B are conceptual diagrams illustrating an example delivery device including a hydraulically driven helical coil.
Figure 21B:
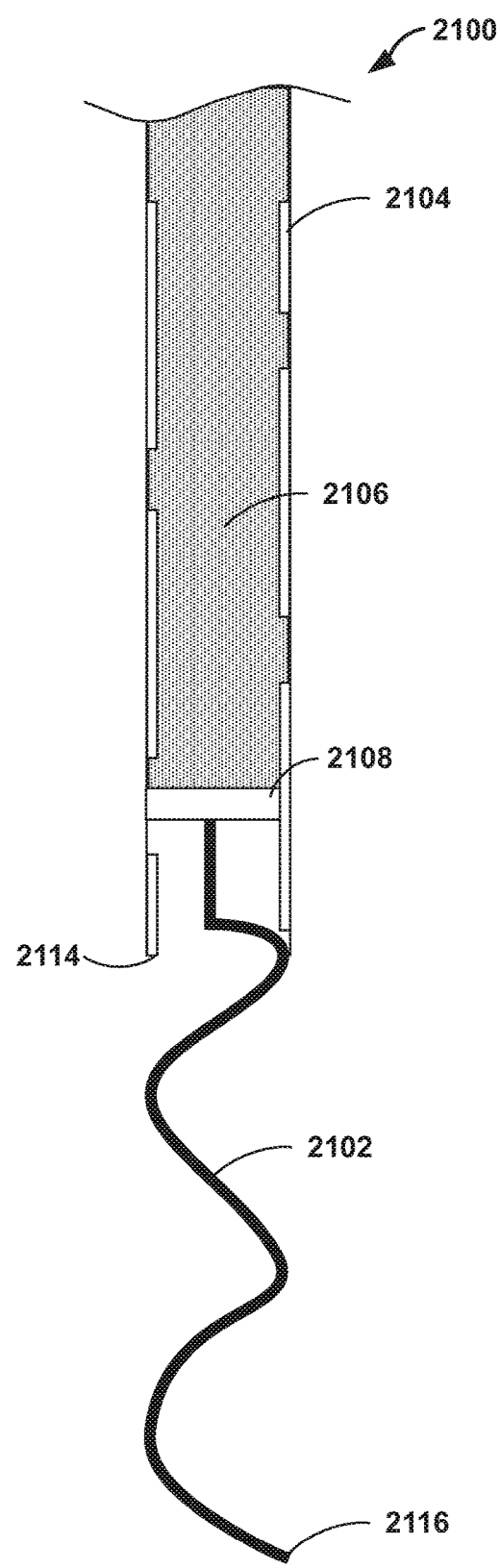

FIGS. 21A and 21B are conceptual diagrams illustrating an example delivery device 2100 including a hydraulically driven helical coil 2102, which may be formed from a shape memory material and may define an incisive distal end 2116 configured to penetrate through tissue of a patient. Delivery device 2100 includes a catheter 2104 including a hydraulic chamber 2106 and a plunger 2108. In some examples, an interior surface 2110 of hydraulic chamber 2106 may include threads 2112 (e.g., spiral grooves). Plunger 2108 may be configured to interface with threads 2112 such that introduction of a hydraulic fluid into hydraulic chamber 2106 may cause plunger 2108 to advance toward a distal end 2114 of catheter 2104 while rotating so as to follow threads 2112. In this way, helical coil 2102 may be advanced from distal end 2114 while controlling a rotation of helical coil 2102 in a first direction. In some examples, extracting the hydraulic fluid for hydraulic fluid chamber 2106 may cause helical coil to withdraw into catheter 2104 while rotating in a second direction opposite the first direction. In this way, medical device 2100 may be configured to drive and rotate a helical coil or needle into tissue. In some examples, medical device 2100 may be used to rotate helical needle 2004 into the tissue to deliver suture 2202 and then rotate helical needle 2004 back out of the tissue, leaving suture 2002 in the tissue.

Figure 22:
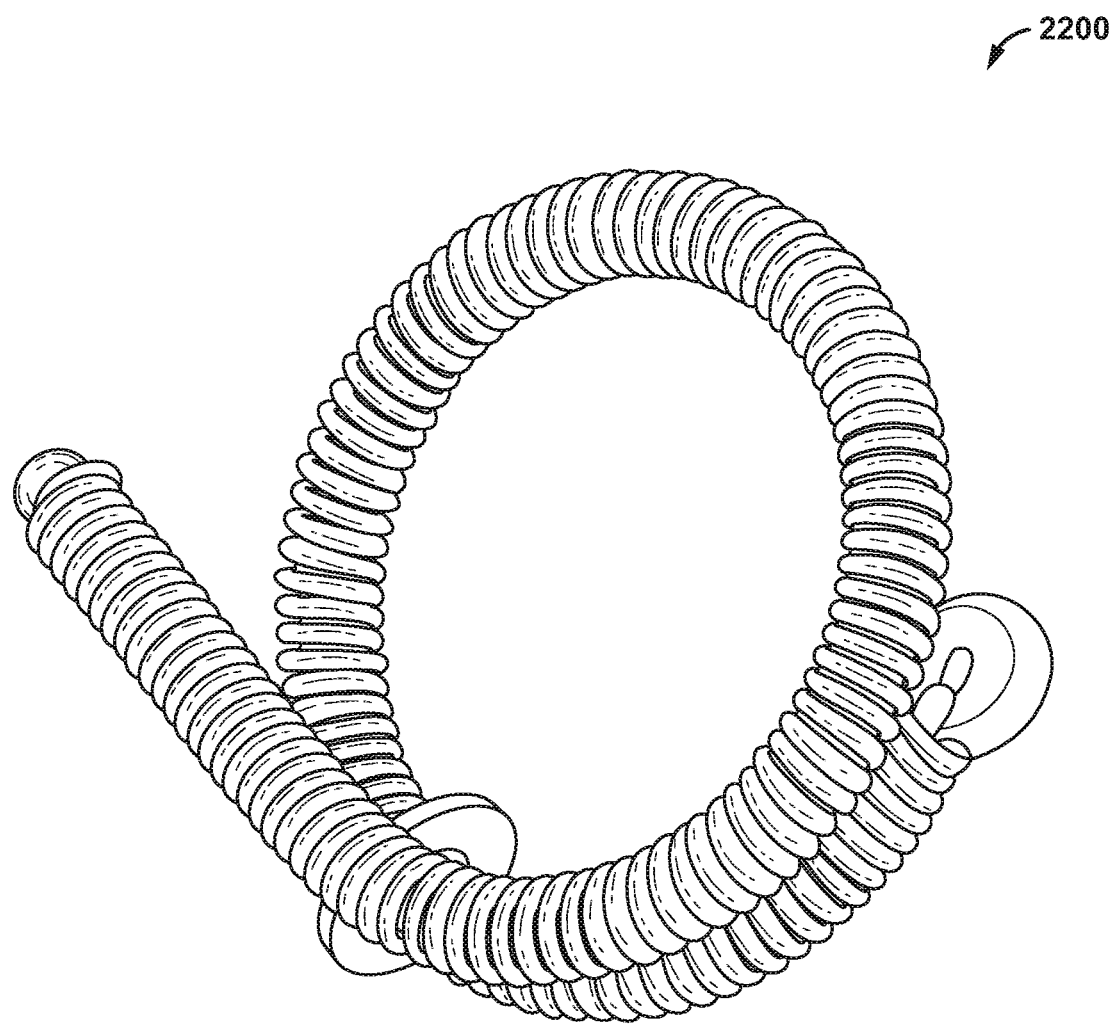
FIG. 22 is a conceptual diagram illustrating an example u-clip configured to clamp leaflets of mitral valve.
Figure 23:
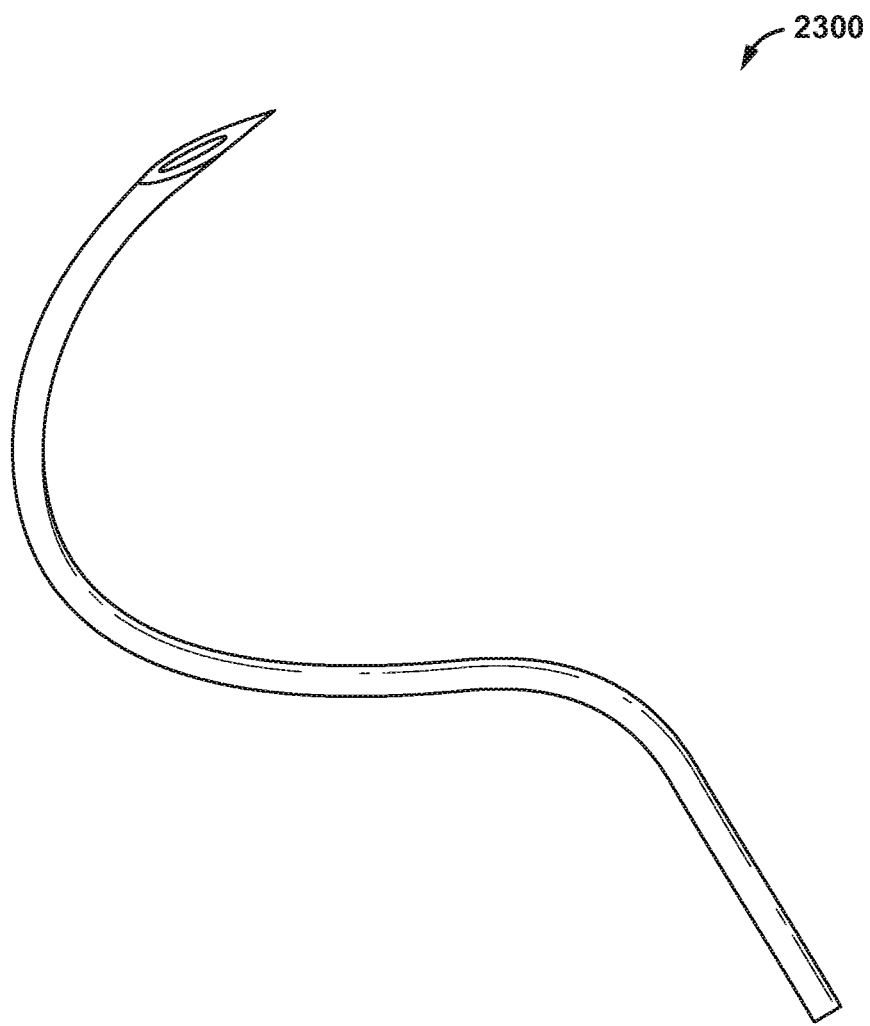
FIG. 23 is a conceptual diagram illustrating a curved, hollow needle configured to deliver a u-clip.

FIG. 22 is a conceptual diagram illustrating an example u-clip 2200 configured to clamp leaflets of mitral valve MV. U-Clips could be used in parallel or series on a catheter to secure the anterior and posterior leaflets together. FIG. 23 is a conceptual diagram illustrating a curved, hollow needle 2300 configured to deliver u-clip 2200. In other examples, a u-clip may be delivered from a straight, hollow needle. Clip 2200 is configured such that after it is deployed from needle 2300 (or a straight needle), clip 2200 coils, securing the two leaflets together. Multiple coils on a single u-clip could be present to help prevent dehiscence.

Various examples have been described. Any combination of the described systems, devices, operations, or functions is contemplated. These and other examples are within the scope of the following claims.

What is claimed is:

1. A medical system comprising: a catheter configured to access vasculature of a patient, the catheter comprising: a handle comprising a control member; and an elongate body, a proximal end of the elongate body being mechanically coupled to the handle; and a plurality of extension members extending from a distal end of the elongate body of the catheter, each of the extension members comprising: a plurality of clamps configured to hold leaflets of a native mitral valve; and at least one actuation member controllable at the control member of the handle and configured to move the plurality of clamps of each of the extension members from an open configuration to a closed configuration to engage the leaflets; and a helical coil configured to join the leaflets of the native mitral valve; wherein each of the extension members plurality of clamps are configured to be removed from the leaflets after the helical coil has been deployed to join the leaflets.

2. A medical device comprising: an elongate body; a plurality of extension members extending from a distal end of the elongate body; each extension member comprising: a plurality of clamps, wherein the plurality of clamps are configured to hold leaflets of a native mitral valve; and a helical coil configured to join the leaflets of the native mitral valve, wherein the plurality of clamps are configured to be removed from the leaflets after the helical coil has been deployed to join the leaflets.

3. The medical device of claim 2, wherein the helical coil includes a straightened delivery configuration within the elongate body, and wherein upon advancement from the distal end of the elongate body, the helical coil assumes a deployed, helical shape.

4. The medical device of claim 2, wherein the plurality of clamps comprise a respective hinge configured to move between an open configuration and a closed configuration.

5. The medical device of claim 4, including at least one actuation member configured to move the plurality of clamps from the open configuration to the closed configuration to hold the leaflets.

6. The medical device of claim 5, wherein the at least one actuation member comprises at least one of a push wire, a pull wire, a bar linkage, or a hydraulic linkage.

7. The medical device of claim 2, wherein the plurality of clamps comprise:
a first clamp configured to engage an anterior leaflet of the native mitral valve of a heart of a patient; and
a second clamp configured to engage a posterior leaflet of the native mitral valve.

8. The medical device of claim 7, further including at least one actuation member having a first actuation member configured to actuate the first clamp, and a second actuation member configured to actuate the second clamp.

9. The medical device of claim 2, further comprising an outer sheath, wherein the elongate body is positioned in sliding engagement with the outer sheath, and wherein, when positioned at a target treatment site, the outer sheath may be withdrawn to expose the plurality of extension members.

10. The medical device of claim 2, wherein the distal end of the elongate body comprises a first extension member coupled to a first clamp of the plurality of clamps and a second extension member coupled to a second clamp of the plurality of clamps.

11. The medical device of claim 2, wherein the plurality of clamps comprise a radiopaque material.

* * * * *